(12) United States Patent
Otto et al.

(10) Patent No.: US 11,766,295 B2
(45) Date of Patent: Sep. 26, 2023

(54) SYSTEM AND METHOD FOR CATHETER-BASED INTERVENTION

(71) Applicant: MATERIALISE NV, Leuven (BE)

(72) Inventors: Clare Otto, Plymouth, MI (US); Janelle Schrot, Plymouth, MI (US)

(73) Assignee: MATERIALISE NV, Leuven (BE)

( * ) Notice: Subject to any disclaimer, the term of this patent is extended or adjusted under 35 U.S.C. 154(b) by 0 days.

(21) Appl. No.: 18/151,931

(22) Filed: Jan. 9, 2023

(65) Prior Publication Data

US 2023/0157760 A1 May 25, 2023

Related U.S. Application Data

(63) Continuation of application No. 16/796,602, filed on Feb. 20, 2020, now Pat. No. 11,571,257, which is a continuation-in-part of application No. PCT/US2019/057295, filed on Oct. 21, 2019.

(30) Foreign Application Priority Data

Oct. 22, 2018 (NL) ...................... 2021849

(51) Int. Cl.
*A61B 34/10* (2016.01)
*A61B 17/00* (2006.01)

(52) U.S. Cl.
CPC .... *A61B 34/10* (2016.02); *A61B 2017/00292* (2013.01); *A61B 2017/00331* (2013.01); *A61B 2034/102* (2016.02); *A61B 2034/105* (2016.02); *A61B 2034/107* (2016.02)

(58) Field of Classification Search
None
See application file for complete search history.

(56) References Cited

U.S. PATENT DOCUMENTS

| | | | |
|---|---|---|---|
| 2005/0107688 A1 | 5/2005 | Strommer | |
| 2007/0043285 A1 | 2/2007 | Schwartz | |
| 2007/0249911 A1 | 10/2007 | Simon | |
| 2008/0160489 A1 | 7/2008 | Brujins | |
| 2010/0071693 A1 | 3/2010 | Mlum | |
| 2010/0076305 A1* | 3/2010 | Maier-Hein | A61B 6/12 600/426 |
| 2010/0142788 A1* | 6/2010 | Matsumoto | G06T 15/08 382/131 |
| 2014/0221821 A1 | 8/2014 | Patwardhan | |
| 2016/0008271 A1 | 1/2016 | Lee | |
| 2016/0038246 A1 | 2/2016 | Wang et al. | |
| 2017/0056116 A1* | 3/2017 | Kostrzewski | G16H 40/63 |
| 2017/0258526 A1 | 9/2017 | Lang | |
| 2018/0125581 A1 | 5/2018 | Wang et al. | |
| 2019/0000551 A1 | 1/2019 | Sone | |

FOREIGN PATENT DOCUMENTS

| | | |
|---|---|---|
| CN | 104095654 | 10/2014 |
| WO | 2018002250 A1 | 1/2018 |
| WO | 20200086495 A1 | 4/2020 |

* cited by examiner

*Primary Examiner* — Andrew G Yang
(74) *Attorney, Agent, or Firm* — Dinsmore & Shohl LLP

(57) ABSTRACT

Systems and methods for planning delivery of an object via a catheter, such as transseptal delivery of a prosthetic mitral valve to a patient's heart are disclosed.

20 Claims, 16 Drawing Sheets

SYSTEM AND METHOD FOR CATHETER-BASED INTERVENTION

CROSS-REFERENCE TO RELATED APPLICATIONS

This application is a continuation of U.S. patent application Ser. No. 16/796,602, filed Feb. 20, 2020, which is a continuation-in-part of International Application No. PCT/US2019/057295, filed Oct. 21, 2019, which claims priority to Dutch Patent Application No. 2021849, filed Oct. 22, 2018. The content of each of the applications is hereby incorporated by reference in its entirety.

BACKGROUND OF THE INVENTION

Field of the Invention

This application relates to systems and methods for catheter-based intervention. In some embodiments, the application more specifically relates to systems and methods for planning delivery of an object via a catheter, such as transseptal delivery of a prosthetic mitral valve or left atrial appendage occlusion device to a patient's heart.

Description of the Related Technology

The human heart is a complex organ having many working parts which are critical to the proper functioning of the heart to provide blood circulation throughout the human body. The human heart is generally made up of four hollow chambers, the right atrium, the right ventricle, the left atrium, and the left ventricle. One of the keys to a properly functioning heart is the regulation of blood flow through these chambers. Regulation of blood flow through and between these chambers is provided by valves. For example, between the right atrium and the right ventricle, there is an atrioventricular opening.

The tricuspid valve is situated at that opening, and permits blood to move from the right atrium into the right ventricle. The valve opens when the blood pressure on the atrium side is greater than that on the ventricular side. When the valve opens, blood is permitted to flow from the right atrium into the right ventricle. When blood pressure is greater on the ventricle side, the valve closes. When the valve closes, blood is prevented from moving back in the other direction.

In the healthy heart, blood flow is also regulated between the left atrium and left ventricle. Here, the mitral valve allows blood to enter the left ventricle from the left atrium when the left atrium fills with blood and the pressure within the left atrium increases to a level above that of the left ventricle. When open, blood flows in a downward direction from the left atrium into the left ventricle, where it is pushed out to the rest of the body as part of the greater circulatory process. When a healthy mitral valve closes, blood flow between the two chambers is stopped, and this closing prevents a reversal of blood flow.

Unfortunately, mitral valves do not always function normally. An abnormally functioning mitral valve can lead to severe health problems. One abnormality associated with the mitral valve is mitral regurgitation ("MR"). Mitral regurgitation is a disorder in which the mitral valve does not close properly during contraction of the left ventricle. This causes blood that has passed from the left atrium into the left ventricle to reverse its flow back into the left atrium.

Progressive mitral valve disease may be treated surgically. One surgical option includes the replacement of the mitral valve where the mitral valve is replaced with a prosthetic mitral valve such as a bio prosthetic replacement or a synthetic replacement. Another surgical option includes repair of the mitral valve. Although mitral valve repair is generally seen as preferable to mitral valve replacement due to the less invasive nature of the procedure, both options may require open-heart surgery. Because many candidates for mitral valve replacement and repair are not good candidates for tolerating the stress of open-heart surgery, there has been ongoing research in the field of transcatheter mitral valve replacement (TMVR). Using TMVR, a prosthetic mitral valve can be introduced using a catheter-based system, obviating the need for an open-heart surgical procedure.

For example, the prosthetic mitral valve may be placed inside a beating heart via a catheter at the bottom of the heart through a tube inserted in a small incision in the patient's chest. The physician uses the tube to deploy the prosthetic mitral valve and positions it so that it rests over the heart's existing mitral valve. Using catheter-based implant techniques, the physical trauma associated with an open heart surgery may be minimized and more patients may be treated effectively for the mitral regurgitation disorder.

Conventionally, TMVR was performed via thoracotomy and included a direct left atrial and a transapical approach. However, based on a reduction of required sheath size of available prosthetic devices (e.g., a prosthetic mitral valve) and delivery systems, a fully percutaneous approach can now be achieved via the atrial septum, with the valve inserted through either the jugular or, more frequently, the femoral vein (Dvir, D., "Transseptal Instead of Transapical Valve Implantation, Making Mitral Great Again?", in: JACC: Cardiovascular Interventions, Vol. 9, No. 11, 2016).

The left atrial appendage (LAA) is a small pouch in the muscle wall of the left atrium. Scientists have yet to determine what function, if any, the LAA performs. In normal hearts, with each heart cycle, the heart will contract and blood will be squeezed out of the left atrium and the LA towards the left ventricle. However, when a patient has atrial fibrillation, the electrical impulses that control the heartbeat do not travel in an orderly fashion through the heart. Instead, many impulses begin at the same time and spread through the atria. The fast and chaotic impulses do not give the atria time to contract and/or effectively squeeze blood into the ventricles. Because the LAA is a little pouch, blood collects there and can form clots in the LAA and atria. When blood clots are pumped out of the heart, they can cause a stroke.

The risk of a stroke can be mitigated by taking a blood thinner. However, these come with inconvenience for the patient, negative side effects and health risks. An alternative is the placement of a left atrial appendage occlusion device (LAAO). This is a parachute-shaped device that is placed at the entrance to the LAA to block any blood flow into and out of the LAA. The standard way of implanting an LAAO device is through a transseptal catheter-based approach. A catheter sheath is inserted into a vein near the groin and guided across the septum (muscular wall that divides the right and left sides of the heart) to the opening of the LAA. The device is placed in the opening of the LAA. This seals off the LAA and keeps it from releasing clots.

There are different methods of selecting the prosthetic device and planning its desired position. However, an equally challenging task is the selection of a delivery system, as not all catheters will be able to follow a trajectory through the patient's heart suitable to deliver the implantable device in the selected location.

SUMMARY

Certain embodiments provide a computer-based method of planning a catheter-based intervention, the method comprising: obtaining, at a computing device, a model of an anatomical region of interest; determining, at the computing device, an entry in the anatomical region of interest; determining, at the computing device, a target in the anatomical region of interest; determining, at the computing device a trajectory from the entry to the target, the trajectory comprising a sequence of a plurality of trajectory segments; and selecting, at the computing device, a catheter from a plurality of catheters based on the catheter being able to achieve the trajectory within at least a threshold.

Certain embodiments provide a computer-based method of planning a catheter-based intervention, the method comprising: obtaining, at a computing device, a model of an anatomical region of interest; determining, at the computing device, an entry in the anatomical region of interest; determining, at the computing device, a target in the anatomical region of interest; selecting, at the computing device, one or more catheters; determining, at the computing device, one or more trajectories for the one or more catheters from the entry to the target based on geometric data about the one or more catheters, each of the one or more trajectories comprising a sequence of a plurality of trajectory segments; and selecting, at the computing device, a catheter from the one or more catheters based on the determined one or more trajectories.

Certain embodiments provide a computer-based method of planning a catheter-based intervention, the method comprising: obtaining, by a computing device, a model of an anatomical region of interest; determining, by the computing device, an entry in the anatomical region of interest; determining, by the computing device, a target in the anatomical region of interest; determining, by the computing device, a trajectory from the entry to the target, the trajectory comprising a sequence of a plurality of trajectory segments, wherein determining a first trajectory segment of the plurality of trajectory segments comprises: obtaining a planned position for an implantable device in the anatomical region of interest; and determining the first trajectory segment as a line segment that connects a first point on a central axis of a first feature of the anatomical region of interest with a second point on a deployment axis of the positioned implantable device and that passes through a geometric center point of a second feature of the anatomical region of interest; and selecting, by the computing device, a catheter from a plurality of catheters based on the catheter being able to achieve the trajectory within at least a threshold Certain embodiments provide a computer-based method of planning a catheter-based intervention, the method comprising: obtaining, by a computing device, a model of an anatomical region of interest; determining, by the computing device, an entry in the anatomical region of interest; determining, by the computing device, a target in the anatomical region of interest; selecting, by the computing device, one or more catheters; determining, by the computing device, one or more trajectories for the one or more catheters from the entry to the target based on geometric data about the one or more catheters, each of the one or more trajectories comprising a sequence of a plurality of trajectory segments, wherein determining at least one trajectory of the one or more trajectories comprises determining the at least one trajectory based on one or more constraints, wherein the one or more constraints comprise one or more operational constraints indicating at least one or more positions within the anatomical region of interest through which the at least one trajectory should pass and one or more tolerances with respect to the one or more positions within which the at least one trajectory should pass; and selecting, by the computing device, a catheter from the one or more catheters based on the determined one or more trajectories.

Certain embodiments provide a computer-based method of planning a catheter-based intervention, the method comprising: obtaining, at a computing device, a model of an anatomical region of interest; determining, at the computing device, an entry in the anatomical region of interest; determining, at the computing device, a target in the anatomical region of interest; determining, at the computing device a trajectory from the entry to the target, the trajectory comprising a parametric or piecewise parametric curve, a sequence of straight line segments, or a combination of curves and line segments; and selecting, at the computing device, a catheter from a plurality of catheters based on the catheter's pre-bent shape closely matching the trajectory.

Certain embodiments provide a non-transitory computer-readable medium having computer-executable instructions stored thereon, which, when executed by a processor of a computing device, cause the computing device to perform the described method.

Certain embodiments provide a computing device comprising a memory and a processor configured to perform the described method.

DETAILED DESCRIPTION OF CERTAIN INVENTIVE EMBODIMENTS

Figure 1:
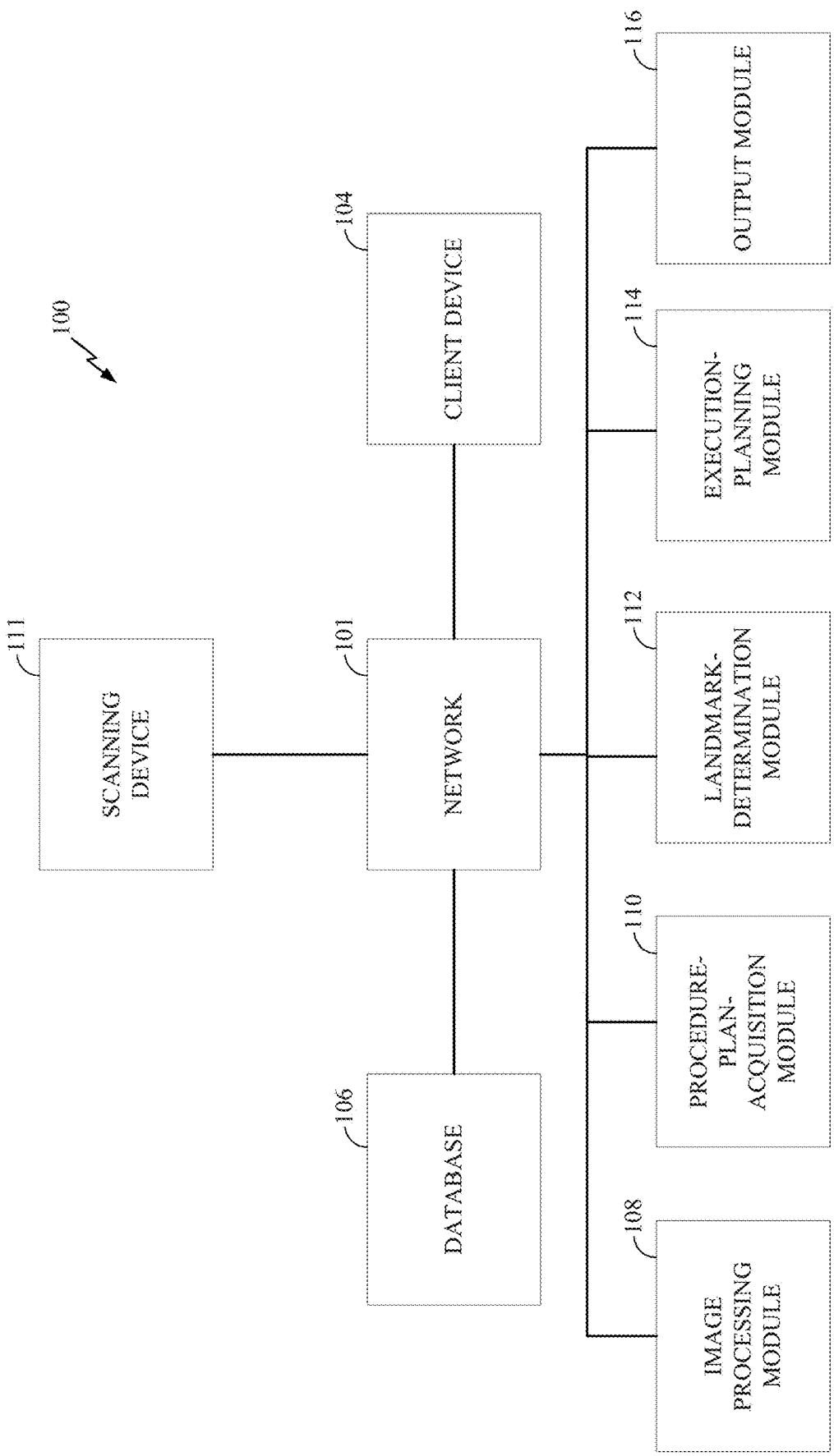
FIG. 1 is a block diagram of one example of a computing environment suitable for practicing various embodiments disclosed herein.

As noted above, selection of a delivery system for delivering a device via a catheter is a challenging task. For example, depending on a patient's anatomy, certain catheters may or may not be used to deliver a device as each catheter has its own max bend and has either one or two bends at a certain distance from the end/each other. This means that it is possible that the incorrect catheter is selected for delivery of a device. During a procedure, accordingly, a medical professional may need to change the catheter when it cannot get to the right location during the procedure, leading to increased time for the procedure in the catheter lab, increased radiation for both staff and patient, and increased waste of materials.

Accordingly, certain embodiments herein provide systems and methods for planning delivery of an object via a catheter, such as transseptal delivery of a prosthetic mitral valve or an LAAO device to a patient's heart. In some embodiments, the systems and methods allow such planning based on the specific anatomy of the specific patient's heart (i.e., patient-specific). In certain embodiments, the systems and methods can be used to see if a certain catheter design (e.g., corresponding to a certain catheter type, model, and/or size) fits the patient anatomy and is thus an option to deliver a device on the location in the heart that it needs to be deployed in. The systems and methods improve the technical field of medicine by allowing for better catheter selection, which can reduce procedure time, leading to less radiation, less waste of materials, less chance of infection, and improved outcome. The systems and methods further improve the functioning of a computing device in that it provides a specific method for planning delivery of an object that reduces computational complexity and use of compute cycles. Further, the systems and methods allow for elimination of the need to generate physical 3D printed models of anatomy to test catheters. The systems and methods can further be used to determine what percentage of a population that a certain catheter design can statistically be used for, or used to develop new catheter designs that work for a larger portion of the population.

In certain embodiments, the systems and methods operate by making a digital model of the anatomy of the patient. A digital model of the device is then placed in the digital model of the anatomy of the patient in one or more possible positions (e.g., location+orientation (e.g., angulation)). For example, a planned position for an implantable device, as in the digital model of the device, may be obtained via input from a user on a computing device, or automatically determined by a computing device based on the digital model of the anatomy. The digital model of the device may comprise a lifelike 3D virtual model of the device, may comprise a stylized representation (e.g. comprising one or more primitive shapes, such as cylinders, spheres, hemispheres, etc.), or may comprise an abstract representation, such as a local coordinate system. The placement of the device in the one or more possible positions can be used to determine constraints on the distal end (e.g., furthest point the tip/end of the catheter is inserted into the patient) and angulation of the catheter. In certain embodiments, depending on the type of device, there might be some tolerance as to the constraints on the catheter.

For example, there may be different types of constraints on the catheter. Capability constraints may be a first type of constraint. A capability constraint on the catheter, for example, can refer to how far the catheter can bend, how far it can reach, where it can bend along the catheter, etc., and is independent of the anatomy in which the catheter is used. In certain aspects, no tolerances are taken into account for such capability constraints. Rather, the systems and methods assume that the catheter cannot exceed the capability constraints.

Operational constraints are a second type of constraint. Operational constraints, for example, can refer to where the catheter should go in the anatomy during a procedure/operation such as where and in what direction the catheter should pass through the anatomy. In certain aspects, tolerances are taken into account for such operational constraints. For example, an operational constraint can comprise the catheter needing to pass through the fossa ovalis (FO). For planning purposes, the constraint may further be the catheter goes through the center of the FO, and that the catheter approaches the FO perpendicularly. However, there may be tolerances for one or more of the position the catheter passes through the FO (e.g., 1 or 2 mm off-center, within 2 mm from the centerline of the inferior vena cava, etc.) or the approach the catheter takes (e.g., within 20° of the normal vector to the FO, etc.).

In further embodiments, the systems and methods then define one or multiple delivery pathway types (e.g., transseptal through femoral vein, transseptal through subclavian vein, etc.) for inserting the catheter and delivering the device. For example, the systems and methods may define specific zones for the catheter to go through (e.g., inferior vena cava (IVC), fossa ovalis, etc.). Different zones may present certain operational constraints (e.g., location, angulation, size, etc.) on the catheter. Different zones may also have different degrees of tolerance as to constraints on the catheter (e.g., bend, curvature, shape, size, endpoint, angulation, etc.).

In further embodiments, the systems and methods fit one or more digital models of one or more catheter designs in the digital model of the anatomy according to the constraints (e.g., operational and/or capability) on how the catheter can deform (e.g., bends at right location, max curvature, etc.) and output which catheter designs can be used for placing the device in the defined position, using the defined delivery pathway, for the specific patient anatomy. The output may be on a UI of a computing device, etc. In some embodiments, the systems and methods automatically select a catheter design.

Though certain embodiments are described with respect to performing transseptal delivery of prosthetic mitral valves or LAAO devices via the inferior vena cava (IVC) as examples, a person skilled in the art will readily appreciate that it also applies to other approaches (e.g. transseptal delivery via the superior vena cava, transapical delivery), other catheter-based interventions (e.g., removal of blood clots, tissue correction, tissue repair, etc.) or delivery systems for other devices, e.g. in other anatomical parts, etc. In certain embodiments, the systems and methods are configured for planning the delivery of a prosthetic valve into a patient's heart. In some embodiments, this may more specifically be the delivery of a prosthetic mitral valve. In some embodiments, this may more specifically be the transseptal delivery of a prosthetic mitral valve, or even more specifically the transseptal delivery of a prosthetic mitral valve via the IVC or via the superior vena cava (SVC). In certain embodiments, the systems and methods are configured for planning the delivery of an LAAO device into a patient's heart. In some embodiments, this may more specifically be the transseptal delivery of an LAAO device, or even more specifically the transseptal delivery of an LAAO device via the IVC or via the superior vena cava (SVC). A person skilled in the art will readily appreciate that all embodiments described herein referencing the IVC also apply, mutatis mutandis, to the SVC. A person skilled in the art will readily appreciate that all embodiments described herein with respect to the delivery of a prosthetic valve also apply, mutatis mutandis, to the delivery of an LAAO device and vice versa.

In certain embodiments, the term "catheter" may refer to any single-component or multi-component tube-like system for insertion into a patient's body to treat diseases or perform a procedure. It may refer to any of the objects known in the art as guides, guiding catheters, delivery systems, shafts, sheaths, dilators, diagnostic catheters, micro-catheters, intermediate catheters or combinations of the same.

In certain embodiments, the systems and methods described herein are described with respect to an anatomical region of interest (e.g., corresponding to one or more anatomical parts) in a static state. However, the systems and methods may also be applicable to anatomical regions of interest that vary in shape over time. For example, one or more steps in the methods described herein or performed by the systems described herein may be repeated for multiple variations of a shape of an anatomical region over time. For example, if the anatomical region of interest is a heart or part of a heart, one or more steps may be repeated for different stages of the heart cycle, e.g., once for the systole and once for the diastole. In certain embodiments, a catheter may be selected that the systems and methods find suitable for all of the variations in shape (e.g., stages).

In certain embodiments herein, a user, such as a clinician, engineer, technician, medical professional, non-medical user, etc., may operate a computing device to perform the methods described herein. Further, the computing device itself may automatically (in part or fully) perform the methods herein. Further, the systems herein may refer to one or more computing devices configured to perform the methods and techniques discussed herein and/or one or more non-transitory computer readable mediums storing instructions to perform the methods and techniques discussed herein.

The systems and methods described herein may be implemented in a computing environment comprising one or more computing devices configured to provide various functionalities. FIG. 1 is an example of a computer environment 100 suitable for implementing certain embodiments described herein. The computer environment 100 may include a network 101. The network 101 may take various forms. For example, the network 101 may be a local area network installed at a surgical site. In some embodiments, the network 101 may be a wide area network such as the Internet. In other embodiments, the network 101 may be a combination of local area networks and wide area networks. Typically, the network will allow for secured communications and data to be shared between various computing devices. Among these computing devices are a client device 104. The client device 104 may be a typical personal computer device that runs an off-the-shelf operating system such as Windows, Mac OS, Linux, Chrome OS, or some other operating system. The client device 104 may have application software installed to allow it to interact via the network 101 with other software stored on various other modules and devices in the computing environment 100. This application software may take the form of a web browser capable of accessing a remote application service. Alternatively, the application software may be a client application installed in the operating system of the client device 104. Client device 104 may also take the form of a specialized computer, specifically designed medical imaging work, or even more specifically for planning delivery of an object via a catheter, such as transseptal delivery of a prosthetic mitral valve to a patient's heart. The client device 104 may further take the form of a mobile device or tablet computer configured to communicate via the network 101 and further configured to run one or more software modules to allow a user to perform various methods described herein.

The computer environment 100 may further include database 106. Typically, the database 106 takes the form of a large database. In certain embodiments, the database 106 is configured to store data pertaining to one or more catheters. The data may include an identification of each catheter and/or may describe the technical capabilities of each catheter. In certain embodiments, the technical capabilities comprise one or more of catheter-specific geometric information, such as the catheter's dimensions, the locations and shapes of any bends along its length, the locations along its length where the catheter's operator may control its bending and/or the range of motion and curvature of each of these bends. In certain embodiments, the catheter-specific information may comprise a virtual 3D model of the catheter, such as one or more of a surface model, a 3D curve representing the catheter's centerline, a radius, or a diameter. For example, the database may comprise data relating to one or more delivery sheaths, each with a predetermined shape.

In certain embodiments, the database 106 further stores data pertaining to one or more implantable devices. The data may contain an identification of each implantable device. In certain embodiments the database 106 further stores compatibility data, describing which implantable devices are compatible with which catheters. The data may further contain geometric information, such as the device's shape and/or dimensions, a virtual 3D model of the device, a schematic representation of the device, and/or its deployment axis.

In certain embodiments, the database 106 is configured to store image files received from a medical imaging machine (e.g., scanning device 111), a picture archiving and communication system (PACS) system, or another form of file transfer. For example, the images may be uploaded by the user from a data carrier to a standalone module or a web-based portal.

These images may be DICOM images, or other types of images such as medical images of the relevant anatomy, e.g. the patient's heart or portions of the patient's heart, or of a virtual 3D model of the relevant anatomy, e.g. a virtual 3D model of the patient's heart, of a portion of the patient's heart, of the blood pool volume of the patient's heart or a portion thereof, etc. In certain embodiments, virtual 3D models may be received through any form of file transfer. For example, virtual 3D models may be uploaded by the user from a data carrier to a standalone module or to a web-based portal. In certain embodiments, the client device 104 includes an anatomical data reception module (e.g., a network interface card (NIC)) configured to receive data pertaining to an individual patient's anatomy, such as from database 106, via a file transfer, from a medical imaging machine, from a PACS system, etc.

In certain embodiments, the database 106 may be part of a scanning device 111, or alternatively it may be part of a client computing device 104.

The computer environment 100 may also include a scanning device 111. The scanning device 111 may typically be a medical imaging device which scans a patient to create images of their anatomy. In the computing environment 100 shown in FIG. 1, the scanning device 111 may be a CT scanner, an MRI device or an ultrasound device. However, a skilled artisan will appreciate that other scanning technologies may be implemented which provide imaging data that can be used to create three-dimensional anatomical models.

As will be explained in detail below, the scanning device 111 may be configured to create cross-sectional images of a patient's heart. In certain aspects, those images may be stored in the database 106, and utilized to create three-dimensional models of the heart. To that end, the computing environment 100 may also include an image processing module 108 (e.g., a segmentation module). The image processing module 108 may take the form of computer software, hardware, or a combination of both which retrieves medical imaging data (e.g., from database 106) and generates a three-dimensional model using stacks of 2-D image data. The image processing module 108 may be a commercially available image processing software for three-dimensional design and modeling such as the Mimics application from Materialise NV. However, other image processing software may be used. In some embodiments, the image processing module 108 may be provided via a web-based network application that is accessed by a computer over the network (such as client device 104, for example). Alternatively, the image processing module may be a software application that is installed directly on the client device 104 (e.g., and accesses database 106 via the network 101). In general, the image processing module 108 may be any combination of software and/or hardware located within the computing environment 100 which provides image processing capabilities on the image data.

In certain embodiments, the image processing module 108 allows conversion of medical images into one or more virtual 3D models of the relevant anatomy. This process can be automated by means of any automatic segmentation method known in the art. Alternatively or additionally this can be a manual process comprising thresholding, filtering, local mask editing operations, image processing techniques and the like.

The computing environment also may include a procedure-plan-acquisition module 110. The procedure-plan-acquisition module 110 is configured to allow a user to, or automatically, plan the placement of an implantable device. The procedure-plan-acquisition module 110 is further configured to allow a user to, or automatically, create a plan (referred to as a procedure plan) based on medical images and/or a virtual 3D model of the relevant anatomy stored in database 106, generated by image processing module 108, and/or acquired by the data reception module. In certain embodiments, the procedure-plan-acquisition module 110 is configured to generate a selection of an implantable device, e.g. selected from the devices stored in database 106, and its planned position and orientation within the patient's anatomy. Alternatively or additionally, the procedure-plan-acquisition module 110 is configured to receive a procedure plan from a file. As with the image processing module 108, the procedure-plan-acquisition module 110 may be a network-based application which is accessed via a web browser by one or more client devices 104. It may also be a native application installed into the operating system of a computer, such as client device 104 for example. In still other embodiments, the procedure-plan-acquisition module 110 may be a network application which is run as a client/server implementation.

The computing environment 100 also may include a landmark-determination module 112. The landmark-determination module 112 is configured to allow a user and/or one or more automatic processes to determine one or more anatomical landmarks for planning the delivery of the implantable device, such as anatomical features, chambers, lumina, surfaces, points, edges, borders, protrusions, indentations, etc., or derived landmarks, such as best-fit planes, centerlines, etc. Automatic processes may be implemented using any suitable feature-recognition algorithms known in the art. The landmarks may be indicated manually and/or determined automatically on the virtual 3D model of the anatomy and/or on the medical images. In the case of transseptal delivery of a prosthetic mitral valve, these landmarks may include one or more of: the inferior vena cava (IVC) and/or the opening of the IVC; the geometric center point of the opening of the IVC; the central inflow axis of the IVC; the fossa ovalis; the geometric center point of the fossa ovalis; the central axis of the fossa ovalis; or the deployment axis of the implantable device. In the case of transseptal delivery of an LAAO device, these landmarks may include one or more of: the inferior vena cava (IVC) and/or the opening of the IVC; the geometric center point of the opening of the IVC; the central inflow axis of the IVC; the fossa ovalis; the geometric center point of the fossa ovalis; the central axis of the fossa ovalis; the ostium of the LAA; the geometric center point of the ostium of the LAA; the centerline of the LAA; or the deployment axis of the implantable device.

The IVC may be indicated, automatically determined and/or stored as a 3D tubular shape, such as a cylinder, best fitting the section of the IVC closest to the right atrium.

The opening of the IVC may be indicated, automatically determined and/or stored as a collection of 3D points along its edge (e.g. identified as the region of highest curvature between the IVC and the right atrium), a 3D polyline or a 3D spline curve.

The geometric center point of the opening of the IVC may be indicated, automatically determined and/or stored as the 3D point representing the center of gravity of any 3D representation of the opening of the IVC.

The central inflow axis of the IVC may be indicated, automatically determined and/or stored as a 3D line tangential to the central longitudinal axis of the IVC at its opening in the right atrium.

The fossa ovalis may be indicated, automatically determined and/or stored as a collection of 3D points, a 3D polyline or a 3D spline curve along its edge, as a 3D surface or as a 3D volume.

The geometric center point of the fossa ovalis may be indicated, automatically determined and/or stored as the 3D point representing the center of gravity of any 3D representation of the fossa ovalis.

The central axis of the fossa ovalis may be indicated, automatically determined and/or stored as a 3D line through the geometric center point of the fossa ovalis, perpendicular to the best-fit plane through a 3D representation of the fossa ovalis.

The ostium of the LAA may be indicated, automatically determined and/or stored as a collection of 3D points, a 3D polyline or a 3D spline curve (e.g. identified as the region of highest curvature between the right atrium and the LAA).

The geometric center point of the ostium of the LAA may be indicated, automatically determined and/or stored as the 3D point representing the center of gravity of any 3D representation of the ostium of the LAA.

The centerline of the LAA may be indicated, automatically determined and/or stored as a collection of 3D points, a 3D polyline or a 3D spline curve running longitudinally along the center of the lumen of the LAA.

In certain embodiments, the deployment axis of the implantable device is the preferred axis of delivery for the implantable device to be placed in the position and orientation according to the procedure plan. For example, the implantable device may be represented in the procedure plan as a cylinder with a specific position and orientation in space with respect to the anatomy. The deployment axis of the implantable device is then determined as the 3D line running along the central axis of this cylinder. For example, the implantable device may be represented in the procedure plan as a virtual 3D model of the device with a specific position and orientation in space with respect to the anatomy. The deployment axis of the implantable device may be given as a 3D line or vector with a fixed position with respect to said virtual 3D model. In certain embodiments, the position of the deployment axis of the implantable device with respect to the position of the implantable device may be retrieved from database 106.

Other interventions may require a different set of anatomical landmarks.

As with the image processing module 108, the landmark-determination module 112 may be a network-based application which is accessed via a web browser by one or more client devices 104. It may also be a native application installed into the operating system of a computer such as, client device 104 for example. In still other embodiments, the landmark-determination module 112 may be a network application which is run as a client/server implementation.

The computing environment 100 also may include an execution-planning module 114. The execution-planning module 114 is configured to allow the planning of a delivery trajectory. The delivery trajectory is the trajectory or a part of the trajectory that a catheter should follow through the patient's anatomy. The execution-planning module 114 may allow the choice between different approaches or may allow the user to compare different approaches (e.g. transapical, transseptal through femoral artery, transseptal through subclavian artery, etc.). For example, the execution-planning module 114 may allow planning the delivery of an implantable device from the IVC through the patient's heart to its planned position and orientation. The execution-planning module 114 may be a fully automatic module, a manual module, or a semi-automated module.

In certain embodiments, the execution-planning module 114 takes one or more of the landmarks determined by the landmark-determination module 112 as input.

In certain embodiments, the execution-planning module 114 allows the user to select, or may automatically determine, one or more tolerances. These tolerances express to what extent a catheter trajectory (delivery trajectory) may deviate from an ideal trajectory. For example, one such tolerance may express to what extent the direction of the most distal section of the catheter may deviate from the direction of the deployment axis of the implantable device in its planned position. The tolerances may be selected based on the type of intervention, the type of device, the medical condition of the patient, etc.

In certain embodiments, the delivery trajectory may comprise a plurality of consecutive line segments. For example, the delivery trajectory may comprise a plurality of consecutive line segments starting at the IVC and ending at the planned location of the implantable device.

Figure 3:
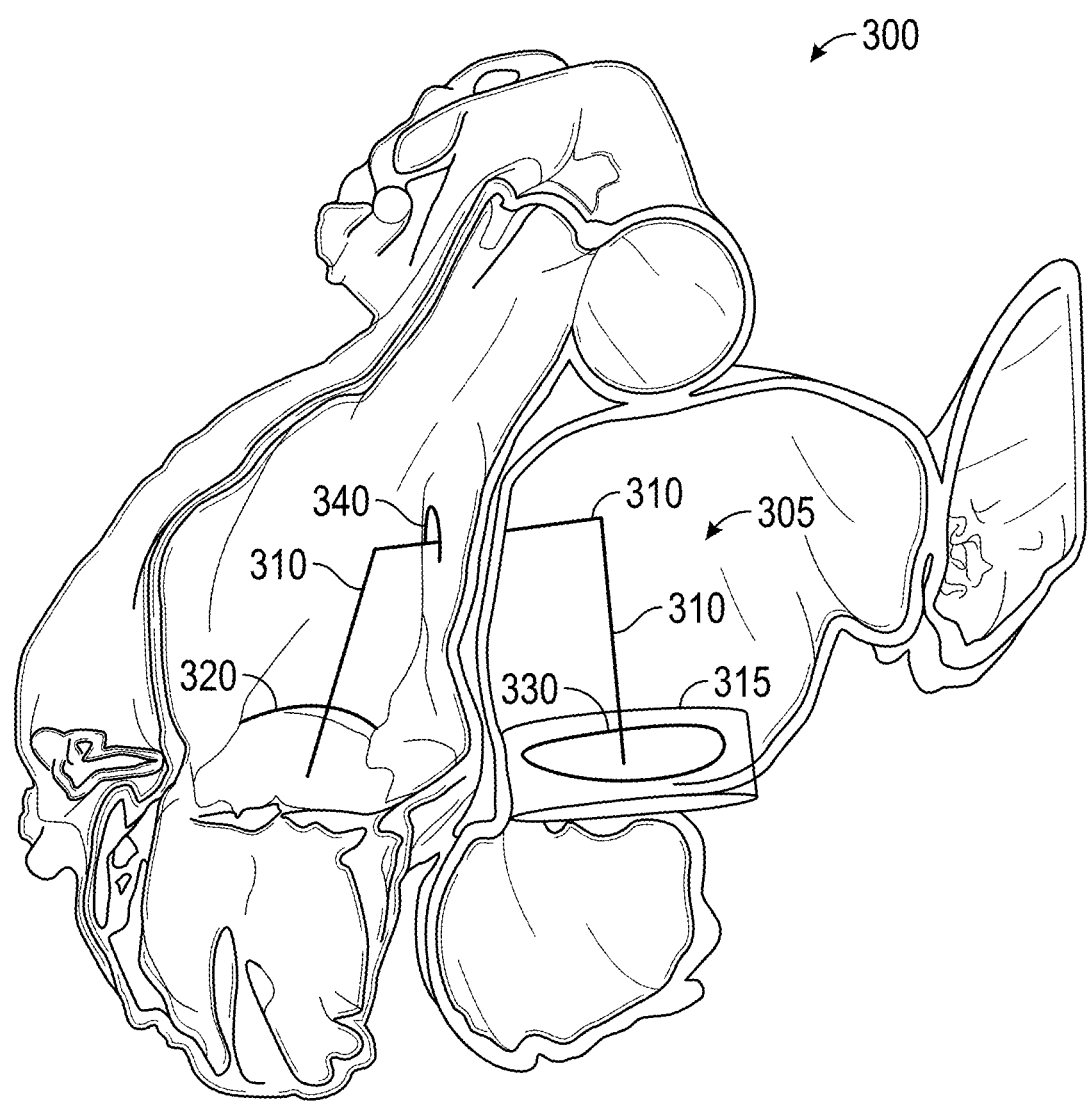
FIG. 3 illustrates a view of an example 3-D model of a heart.
Figure 4:
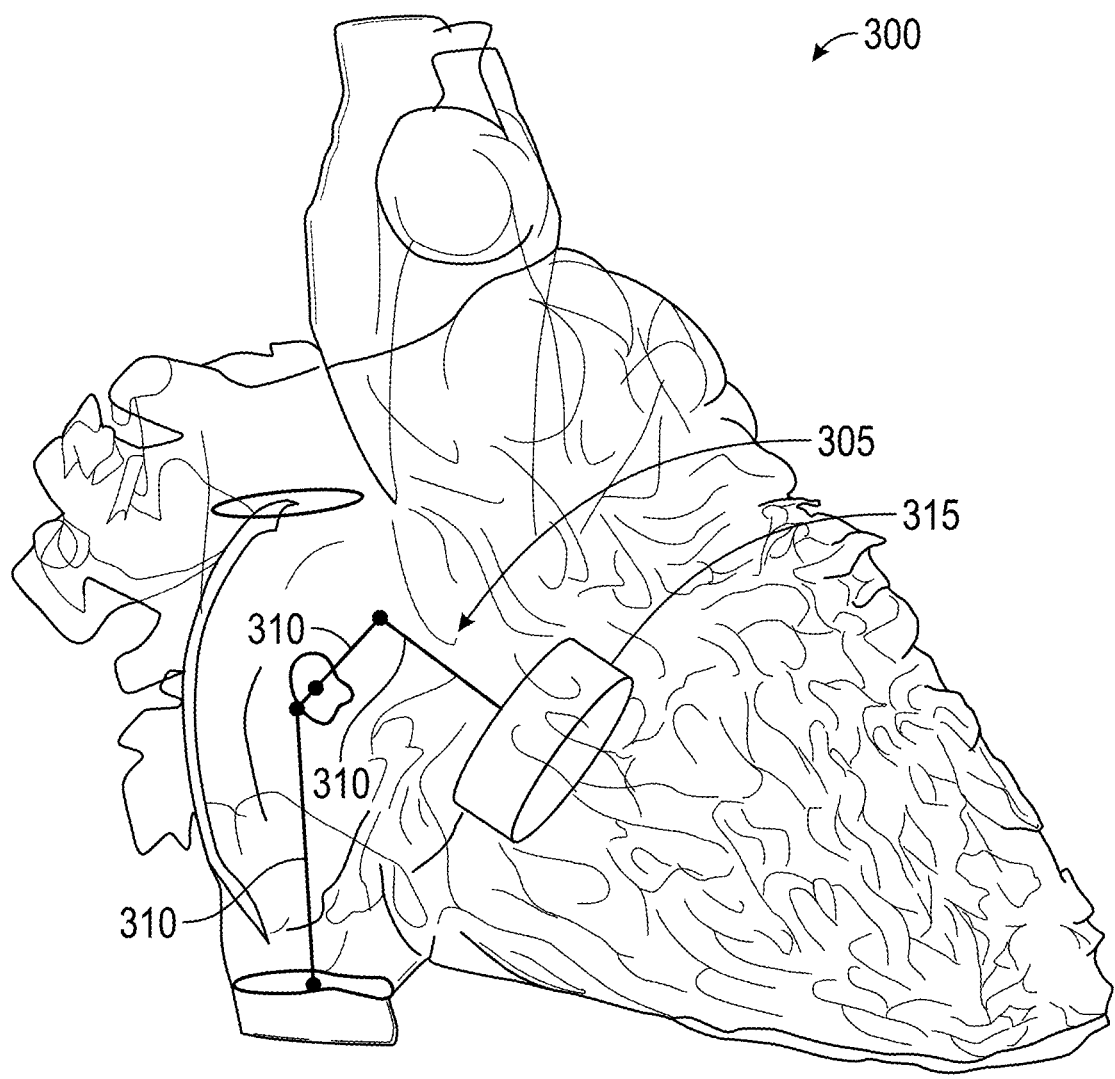
FIG. 4 illustrates a view of an example 3-D model of a heart.

In certain embodiments, the number of line segments is determined by the capabilities of the selected catheter. Many catheters have two locations of controlled bending along their length. They may therefore only be able to execute a trajectory comprising a maximum of three line segments: one before the first bend, one between the bends and one after the second bend. Catheters with more locations of controlled bending may execute trajectories comprising a higher number of line segments. FIGS. 3 and 4 illustrate an image of a patient's heart 300. A delivery trajectory 305 comprising a plurality of line segments 310 and a planned location of an implantable device 315 are shown. It should be noted that though certain embodiments describe outputting a schematic representation of a delivery trajectory, in certain embodiments systems and methods may output (e.g., on a display of a computing device) a model of a catheter in a patient's anatomy corresponding to the procedure and/or delivery trajectory. In other embodiments, the number of line segments is chosen to suit the procedure being planned and the anatomical regions the trajectory has to pass.

It should be understood that though certain embodiments are described herein using straight line segments as forming a delivery trajectory, curves with control points (e.g., parametric or piecewise parametric curves, such as splines, Bézier curves, etc.) may additionally or alternatively be used to form a delivery trajectory. For example, a delivery trajectory may be formed as one or more curves with control points to adjust the curvature of each of the one or more curves. A delivery trajectory may also be formed as a combination of one or more curves and one or more line segments. For example, line segments may be separated by curves that mimic the bending of the catheter. In any combination of curves and/or line segments, the system may enforce $1^{st}$-order, $2^{nd}$-order or $3^{rd}$-order continuity between consecutive segments. The term trajectory segments may be used to refer to line segments and/or such curve(s) as discussed.

For example, FIG. 3 illustrates a virtual 3D model of a patient's heart 300 showing a cut through the patient's heart, revealing both atria and ventricles. On the left is the opening of the IVC in the right atrium, indicated by means of a circle 320 (largely obscured). On the right is the annulus of mitral valve indicated by a 3D spline 330. The planned position of a prosthetic mitral valve 315 is indicated by means of a cylinder. The planned position may be selected by a user on a computing device (e.g., using an input device to define a desired position), determined automatically by the computing device based on the virtual 3D model of the patient's heart 300, etc. The outline of the fossa ovalis is also indicated by means of a 3D spline 340. The trajectory 305 for a catheter for the delivery of the prosthetic mitral valve is indicated as a sequence of three trajectory segments 310 with small spherical handles at the nodes. In certain aspects, a user may modify the trajectory 305 by manipulating the handles. The sequence of trajectory segments 310 may represent any of the trajectories as described herein (e.g., preferred trajectory, catheter-specific optimal trajectory, catheter's best-matching trajectory, any catheter's trajectory). FIG. 4 similarly illustrates a virtual 3D model of the patient's heart 300.

In certain embodiments, planning the delivery trajectory may comprise determining the number of trajectory segments and the lengths, locations, curvatures, and/or directions of each of the plurality of trajectory segments, and selecting one or more catheters from the device database that are capable of executing the delivery trajectory. A distinction may be made between embodiments that involve catheters that comprise locations of controlled bending, such as catheters for placing guide wires, and embodiments that involve catheters with a pre-determined three-dimensional shape, such as device delivery sheaths.

(A) Catheters with Locations of Controlled Bending

In certain embodiments in which the catheters comprise locations of controlled bending, whether a catheter is capable of executing a given delivery trajectory depends in part on one or more of the following three criteria (e.g., applied using the tolerances described above):

1) The number of trajectory segments may not exceed the catheter's number of locations of controlled bending+1.

2) Depending on the design of the catheter, there may be a fixed or maximum distance between consecutive locations of controlled bending. This distance may set a limit to the length of the corresponding trajectory segment. Also depending on the design of the catheter, the relationship between the distance between two consecutive locations of controlled bending and the length of the corresponding trajectory segment may depend on the bending angle, the length of the bend and/or curvature at one or both of the locations of controlled bending.

Figure 3A:
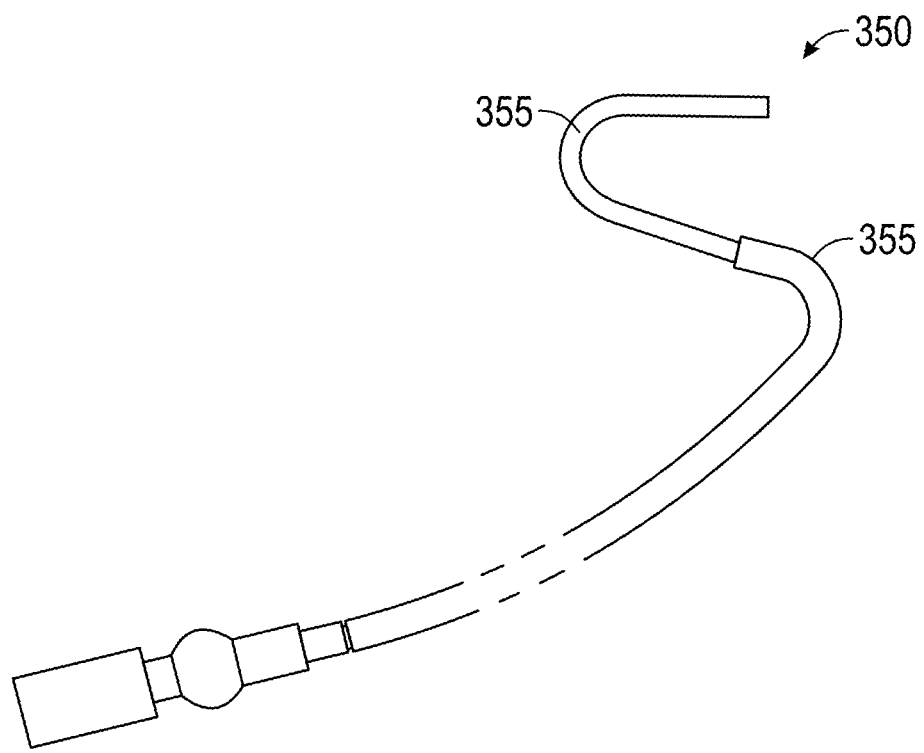
FIG. 3A illustrates an example of a catheter that includes two locations of controlled bending.
Figure 3B:
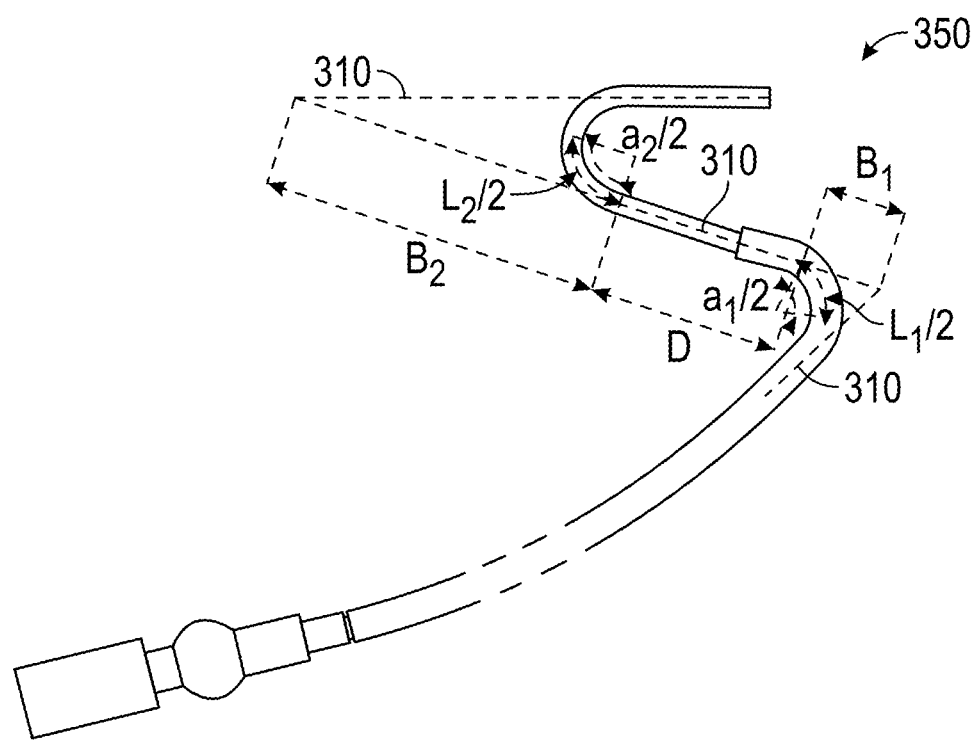
FIG. 3B illustrates trajectory segments representing a trajectory for the catheter of FIG. 3A.

For example, FIG. 3A illustrates an example of a catheter 350 that includes two locations 355 of controlled bending. Further, FIG. 3B illustrates trajectory segments 310 representing a trajectory 305 for the catheter 350. In certain aspects, the length of each of the line segments 305, as shown, depends on the curvature of the adjoining bends at locations 355. For example, assuming that each bend can be approximated by a segment of a circle, the length of the corresponding line segment can be computed as:

$$L_{segment} = B_1 + D + B_2 = \frac{L_1}{\alpha_1} \cdot \tan\left(\frac{\alpha_1}{2}\right) + D + \frac{L_2}{\alpha_2} \cdot \tan\left(\frac{\alpha_2}{2}\right)$$

wherein $L_1$ and $L_2$ are the lengths of the bending portions of the catheter delimiting a straight section, and $\alpha_1$ and $\alpha_2$ are the respective angles over which those portions are bent.

In other aspects, instead of computing the length of a trajectory segment 310 based on the curvature of the adjoining bends at locations 355, arcs can be used to represent the bends at locations 355 and line segments used to represent the straight portions of the catheter 350 between the arcs.

3) Depending on the design of the catheter, there may be a limit to the twisting (e.g., torsion around the longitudinal axis between consecutive locations of controlled bending) and bending (e.g., flexing in a plane comprising the longitudinal axis at a location of controlled bending) angles achievable. These maximal twisting and bending angles may set a limit to the angular degrees of freedom of two or more consecutive trajectory segments.

In certain embodiments determining the delivery trajectory and selecting the one or more suitable catheters may follow a trajectory-first or a catheter-first approach.

In certain embodiments, a trajectory-first approach comprises the following three steps:

1) First a number of trajectory segments is selected (e.g., by a user of the execution-planning module 114 or automatically by the execution-planning module 114). In some embodiments, this number may be fixed to 3. Other embodiments may allow a free selection of a number of 2 or higher. Still other embodiments may determine the number based on which catheters are available (e.g., based on data in database 106), and how many locations of controlled bending they have. In certain embodiments, these embodiments may only consider those catheters that are compatible with the implantable device selected by the procedure-plan-acquisition module 110 if compatibility information is available in the device database 106. It should be noted that selection of an implantable device may refer to selection of different types, models, and/or sizes of implantable devices.

Figure 3C:
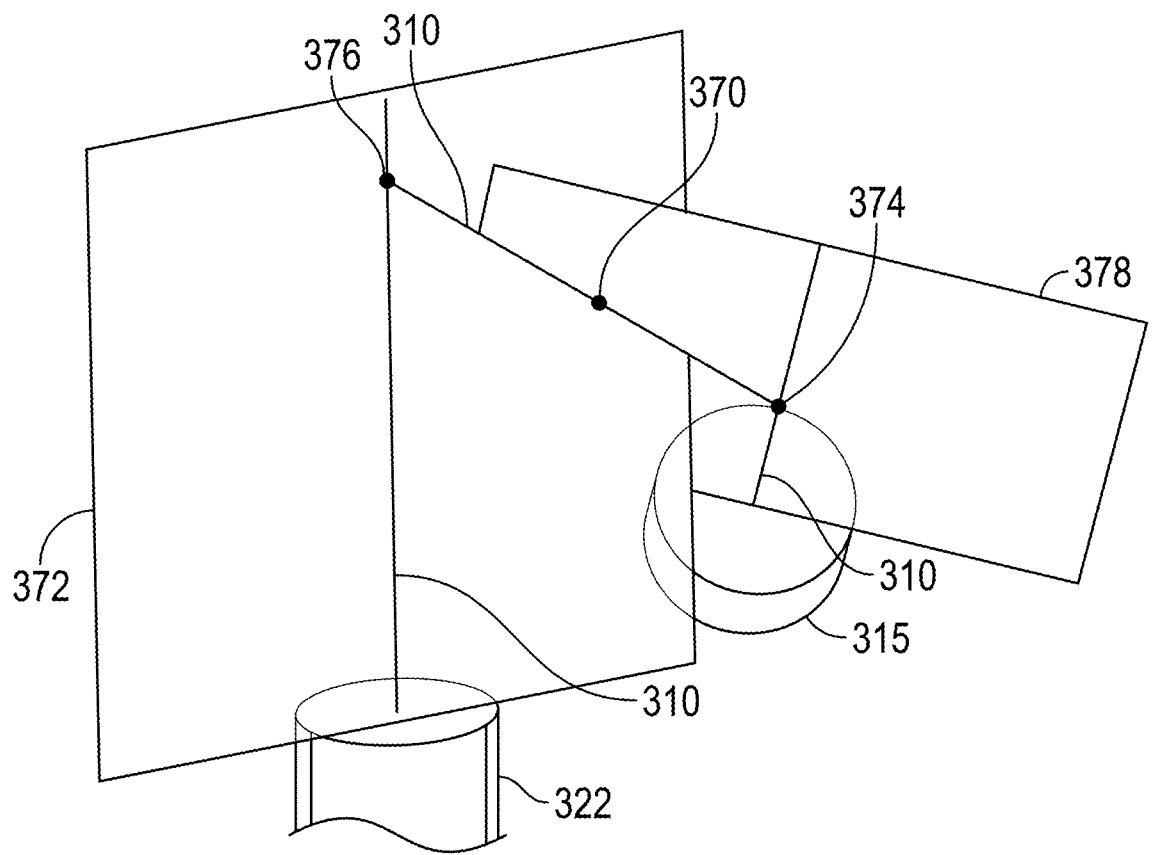
FIG. 3C illustrates the use of planes for determining a trajectory segment.

2) In a next step, a target trajectory—e.g. a preferred sequence of trajectory segments—is determined (e.g., by a user of the execution-planning module 114 or automatically by the execution-planning module 114). In an ideal situation, each of the trajectory segments complies with one or more requirements. For example, a first trajectory segment may start at the IVC and may ideally coincide with the central inflow axis of the IVC, i.e. it has one endpoint in the center of the opening of the IVC in the right atrium and a direction tangential to the central longitudinal axis of the IVC at that point. For example, a second trajectory segment may ideally perforate the fossa ovalis at the geometric center point of the fossa ovalis and may ideally be parallel to the central axis of the fossa ovalis. For example, a third trajectory segment may end at the planned position of the implantable device and may ideally be parallel to the deployment axis of the implantable device. For example, all trajectory segments should be fully contained within the blood pool volume of the heart, except for the section where the second trajectory segment perforates the fossa ovalis. In a typical situation, it may not be possible to reconcile all of these requirements. The execution-planning module 114 may therefore be configured to (e.g., automatically) determine a preferred sequence of trajectory segments based on an order of priority in which these requirements may be relaxed and/or a degree to which these requirements may be relaxed. For example, the execution-planning module 114 may keep the end point and the direction of the third trajectory segment fixed. It may prioritize to first relax the requirement of the second trajectory segment being parallel to the central axis of the fossa ovalis, optionally within a predetermined angular range. It may prioritize to then relax the requirement of the second trajectory segment passing through the geometric center point of the fossa ovalis, optionally within a predetermined distance range. It may prioritize to next relax the requirement of the first trajectory segment being parallel to the IVC inflow axis, optionally within a predetermined angular range. It may prioritize to next relax the requirement of the first trajectory segment having its starting point in the center of the opening of the IVC, optionally within a predetermined distance range. Requirements may be relaxed until a solution can be found. The execution-planning module 114 may use a heuristic approach. Alternatively, the execution-planning module 114 may search for the sequence of trajectory segments that optimizes a certain target function, e.g. the sequence that minimizes a weighted average of how far the requirements need to be relaxed, or the sequence that minimizes the angles between consecutive trajectory segments. Any suitable optimization techniques known in the art may be used to optimize the target function by the execution-planning module 114. Other priorities or combinations of fixed and relaxed requirements are possible. For example, the execution-planning module 114 may keep all requirements fixed except the second trajectory segment being parallel to the central axis of the fossa ovalis. As illustrated in FIG. 3C, the second trajectory segment may then be determined as the trajectory segment that connects a point on the central inflow axis of the IVC 322, represented by a cylinder, with a point on the deployment axis of the implantable device 315, represented by a cylinder, and passes through the geometric center point 370 of the fossa ovalis, represented by a node. This trajectory segment can be determined by constructing a plane 372 through the central inflow axis of the IVC 322 and the geometric center point 370 of the fossa ovalis, then determining the point 374 at which the deployment axis of the implantable device 315 intersects this plane 372, then creating a line through this point 374 and the geometric center point 370 of the fossa ovalis, then determining point 376 where this line intersects the central inflow axis of the IVC and then creating a trajectory segment that connects both intersection points 374 and 376. Alternatively, this trajectory segment can be determined by constructing a plane 378 through the deployment axis of the implantable device 315 and the geometric center point 370 of the fossa ovalis, then determining point 376 at which the central inflow axis of the fossa ovalis 322 intersects this plane 378, then creating a line through this point 376 and the geometric center point 370 of the fossa ovalis, then determining point 374 where this line intersects the deployment axis of the implantable device 315 and then creating a trajectory segment that connects both intersection points 374 and 376. Alternatively, the same result can be obtained by constructing a first plane 372 through the central inflow axis of the IVC 322 and the geometric center point 370 of the fossa ovalis, constructing a second plane 378 through the deployment axis of the implantable device 315 and the geometric center point 370 of the fossa ovalis, determining the intersection line of these two planes, and creating a trajectory segment 310 between the points where this intersection line intersects with the central inflow axis of the IVC 322 and the deployment axis of the implantable device 315. It should be noted that in certain aspects, such as in the claims, reference to a first trajectory segment, second trajectory segment, and third trajectory segment may not correspond to an order of trajectory segments in a trajectory from entry to target. For example, the second trajectory segment as described above (e.g., a segment through a septum), may instead be referred to as a first trajectory segment. Further, the first trajectory segment as described above (e.g., a segment through the right atrium), may instead be referred to as a second trajectory segment. Further, the third trajectory segment as described above (e.g., a segment through the left atrium), may be referred to as a third trajectory segment.

3) Once the preferred trajectory has been determined, the execution-planning module 114 may consult the database 106 and determine for each catheter in the database whether it is able to execute the preferred trajectory. To determine whether a catheter is able to execute the preferred trajectory, the tolerances described above may be applied. As output, the execution-planning module 114 may deliver a list of suitable catheters. Alternatively, the execution-planning module 114 may compute for each catheter in the database to what extent the trajectory would have to deviate from the preferred trajectory and assign a score to each catheter in the database 106, e.g. as a polynomial function of the angles and/or the differences in length between corresponding sections of the preferred trajectory and the catheter's closest-matching trajectory. The coefficients of the polynomial function may penalize certain deviations more than others. As output, the module may deliver a list of catheters, each with a score. The execution-planning module 114 may consider only those catheters that are compatible with the implantable device selected by the procedure-plan-acquisition module 110 if compatibility information is available in the database 106.

Further, in certain aspects, as additional output, the execution-planning module 114 may deliver additional measurements regarding the preferred trajectory and/or catheter, such as a distance between a bend and the FO.

In certain embodiments, a catheter-first approach comprises the following four steps:

1) For each of the catheters in the database 106, the execution-planning module 114 may determine one or more possible trajectories, such as from the IVC to the planned location of the implantable device, based on the catheter-specific geometric information stored in the database 106. The execution-planning module 114 may consider only those catheters that are compatible with the implantable device selected by the procedure-plan-acquisition module 110 if compatibility information is available in the database 106. In certain embodiments, the execution-planning module 114 may determine types of trajectory segments to use for the possible trajectories for a given catheter based on characteristics of the catheter. For example, locations of controlled bending may occupy a certain length of the catheter. This length can be used to more accurately calculate a trajectory or more accurately represent a trajectory.

2) The execution-planning module 114 may evaluate each of the possible trajectories against the requirements described above. For each of the requirements, the trajectory's deviation from the ideal situation may be computed, e.g. as the angle between the IVC's central inflow axis and the corresponding section of the catheter, the angle between the fossa ovalis' central axis and the corresponding section of the catheter, the angle between implantable device's deployment axis and the corresponding section of the catheter, the shortest distance between the center of the opening of the IVC and the axis of the catheter, the distance between the geometric center of the fossa ovalis and the point where the catheter intersects the septum, the distance between center point of the implantable device and the axis of the most distal section of the catheter, etc. When computing the deviations, the execution-planning module 114 may take into account the tolerances describe above, e.g. by only counting a deviation when a distance or angular difference exceeds the corresponding tolerance. A target function may be defined as a polynomial function of these deviations and a catheter-specific optimal trajectory may be determined by using any suitable optimizing algorithm known in the art. The execution-planning module 114 may assign a score to each catheter-specific optimal trajectory, e.g. based on the value of the target function. Limits may be set to the search space, e.g. by imposing maximum values to one or more of the computed deviations, and/or by monitoring that the entire trajectory is entirely contained within the blood pool volume of the right and left atrium.

3) In certain embodiments, catheters that are not able to follow a trajectory from the IVC through the fossa ovalis to the planned position of the implantable device that is entirely contained within the blood pool volume may be filtered out.

4) As output, the execution-planning module 114 may deliver a list of eligible catheters, optionally each with a score.

(B) Catheters with a Pre-Determined 3D Shape

In certain embodiments, the catheters may have a pre-determined 3D shape. More particularly, in certain embodiments, their most distal end may exhibit one or more pre-determined bends. Examples include certain device delivery sheaths. In certain embodiments, such sheaths are flexible enough to be led over a guidewire from the incision to the implantation site. However, in certain embodiments, their pre-determined shape has the purpose to keep them in position even after removal of the guidewire and to facilitate correct device placement.

In certain embodiments determining the delivery trajectory and selecting the one or more suitable catheters may comprise the following two steps:

1) First, a target trajectory—e.g. a preferred parametric curve, piecewise parametric curve or sequence of trajectory segments—is determined (e.g., by a user of the execution-planning module 114 or automatically by the execution-planning module 114). This target trajectory may comply with one or more requirements. For example, the target trajectory or a first trajectory segment may start at the IVC and may be tangential to the central inflow axis of the IVC, i.e. it has one endpoint in the center of the opening of the IVC in the right atrium and a direction tangential to the central longitudinal axis of the IVC at that point. For example, the target trajectory or a second trajectory segment may perforate the fossa ovalis at the geometric center point of the fossa ovalis and may be parallel at the perforation point to the central axis of the fossa ovalis. For example, the target trajectory or a third trajectory segment may end at the planned position of the implantable device and may be parallel at its end point to the deployment axis of the implantable device. Alternatively, the trajectory or a third trajectory segment may end at the geometric center point of the ostium of the LAA and may be parallel at its end point to the centerline of the LAA. For example, the entire trajectory or all trajectory segments should be fully contained within the blood pool volume of the heart, except for the section where the second trajectory segment perforates the fossa ovalis. The target trajectory may be determined automatically based on one or more landmarks determined by the landmark determination module 112 or may be manually indicated by the user.

Figure 7:
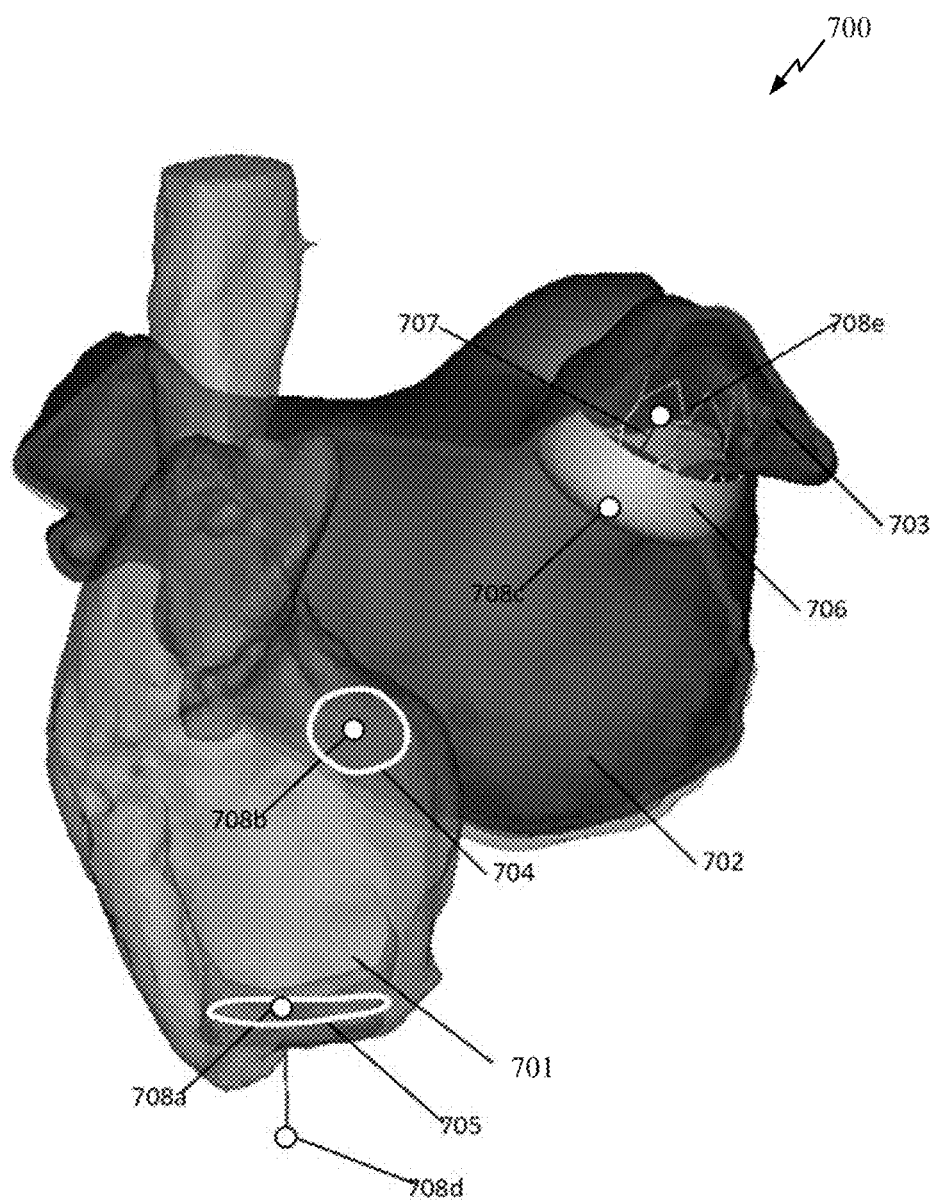
FIG. 7 illustrates a view of an example 3-D model of a heart with a model of an LAAO device in a planned position and control points for determining a target trajectory, according to certain embodiments.
Figure 8:
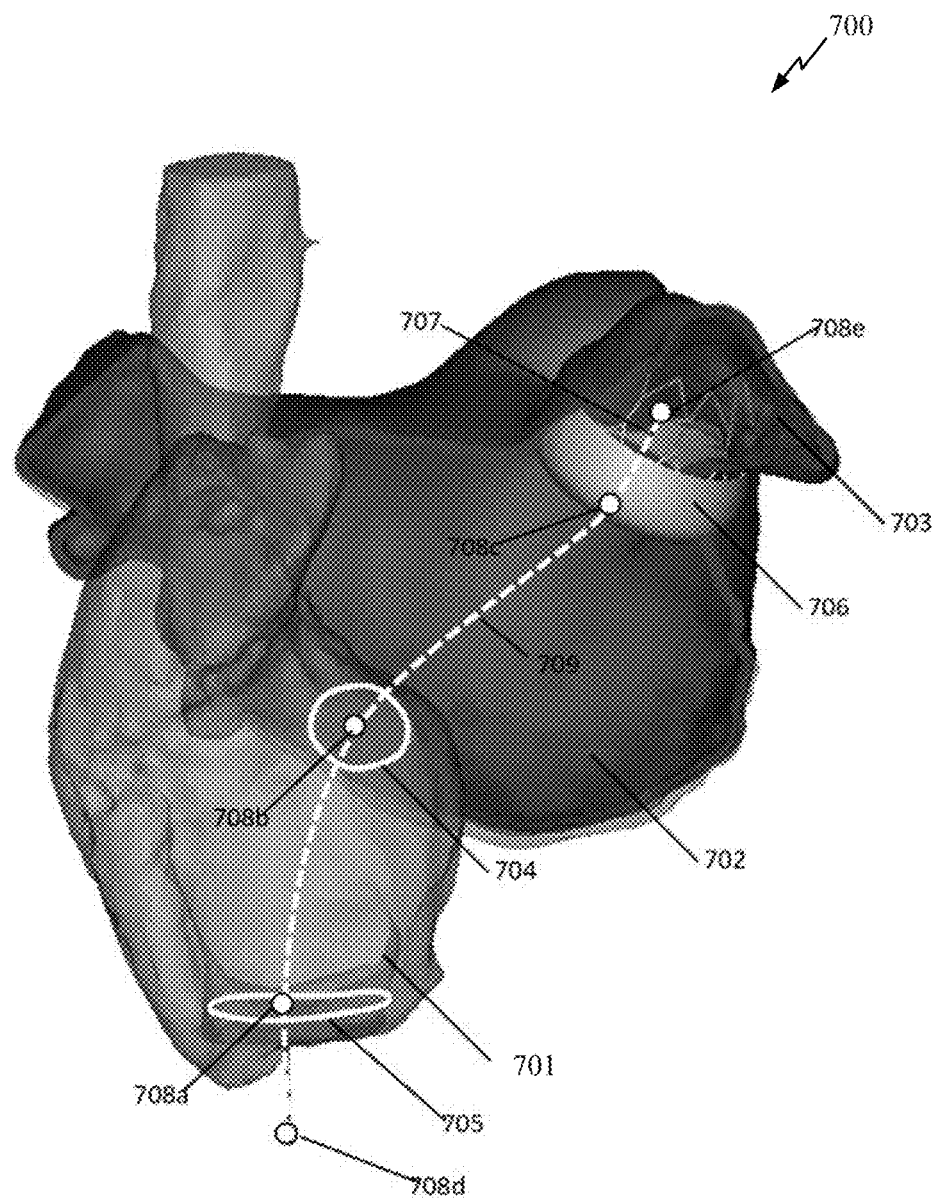
FIG. 8 illustrates the determined target trajectory represented as a spline based on FIG. 7, according to certain embodiments.
Figure 14:
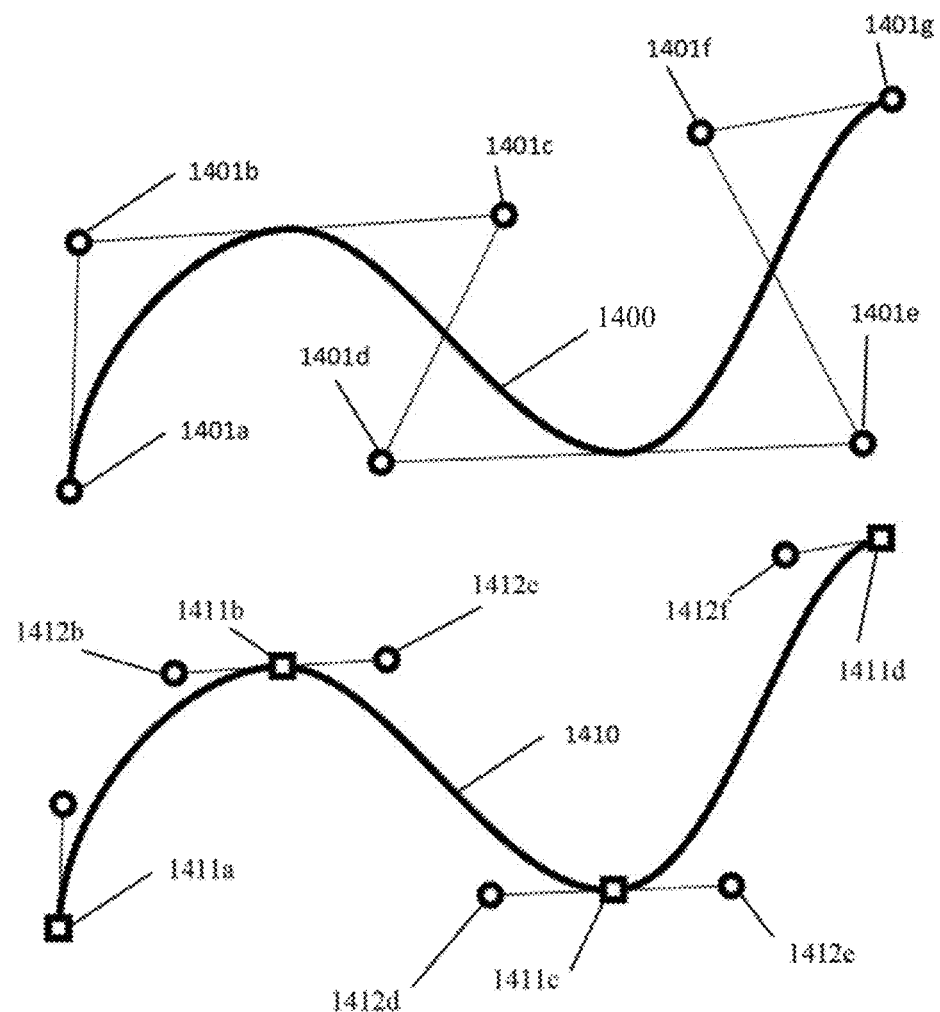
FIG. 14 illustrates two forms of splines, according to certain embodiments.

FIG. 7 illustrates a view of an example 3-D model 700 of a part of a heart with a model of an LAAO device 706 in a planned position and knots 708 for determining a target trajectory, according to certain embodiments. FIG. 7 illustrates a right atrium 701, a left atrium 702, a LAA 703, a FO 704, an opening of the IVC 705, a planned deployment direction 707 of the LAAO device 706, and spline knots 708a-708e. For example, as illustrated in FIG. 7, in the case of the placement of an LAAO device 706, the target trajectory may be determined as a 3D spline curve with a knot in the geometric center point of the opening of the IVC 708a, a knot in the geometric center point of the FO 708b and a knot in the planned location of the LAAO device 708c. Additional knots may be used to control the direction of the spline curve at one or more of these locations. For example, the direction of the spline at the geometric center point of the opening of the IVC can be made substantially parallel to the central inflow axis of the IVC by adding a knot 708d at a certain distance from the center point of the opening of the IVC—such as a distance between 1 cm and 3 cm, such as 2 cm—in the opposite direction, i.e. into the IVC. Similarly, the direction of the spline at the planned location of the LAAO device can be made substantially parallel to the deployment direction of the device by adding a knot 708e at a certain distance from the planned location of the LAAO device—such as a distance between 1 cm and 3 cm, such as 2 cm—in the deployment direction. FIG. 8 shows the resulting spline 709 representing the target trajectory. One or more types of parametric and piecewise parametric curves can be used with embodiments herein, such as splines, Bézier splines, B-splines and/or non-uniform rational B-splines (NURBS), and various definitions and implementations are known in the art, as is illustrated in FIG. 14, showing two identical splines 1400 and 1410, according to an example. Spline 1400 is defined by means of a sequence of control points 1401a-g. Spline 1410 is defined by means of a combination of knots 1411a-d and control points 1412a-f. A person skilled in the art will readily understand that any of these definitions may be used to obtain similar results. For example, the direction of the spline at the geometric center point of the opening of the IVC can be made substantially parallel to the central inflow axis of the IVC by adding a control point at a certain distance from the center point of the opening of the IVC—such as a distance between 1 cm and 3 cm, such as 2 cm—in a direction parallel to the central inflow axis into the right atrium. A similar result may also be obtained with a sequence of straight line segments, with a sequence of curves, such as arcs, parametric curves or piecewise parametric curves, or with a combination of straight line segments and curves. The result of this first step is a preferred trajectory.

Figure 9:
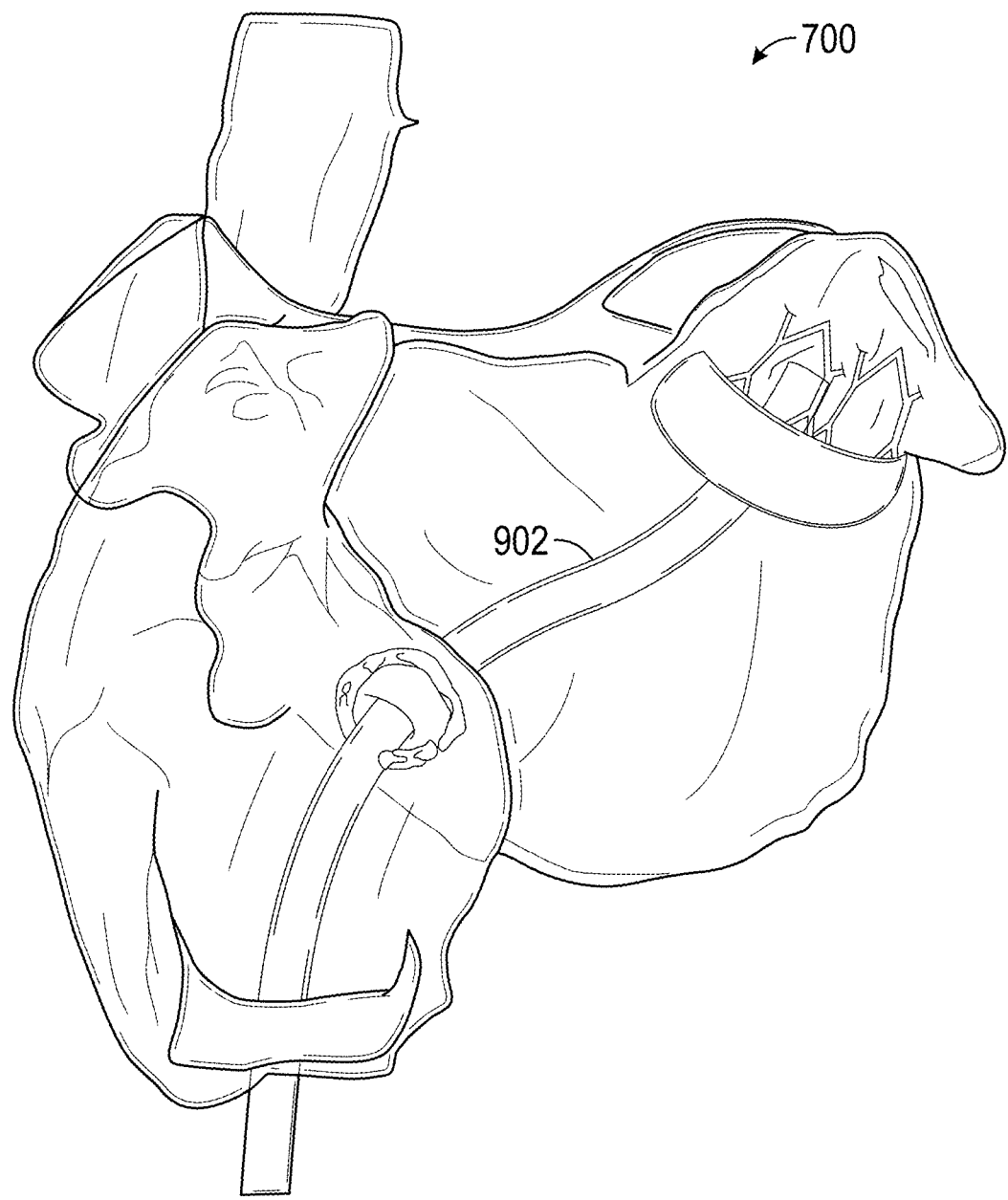
FIG. 9 illustrates the determined target trajectory based on FIG. 7, according to certain embodiments.
Figure 10:
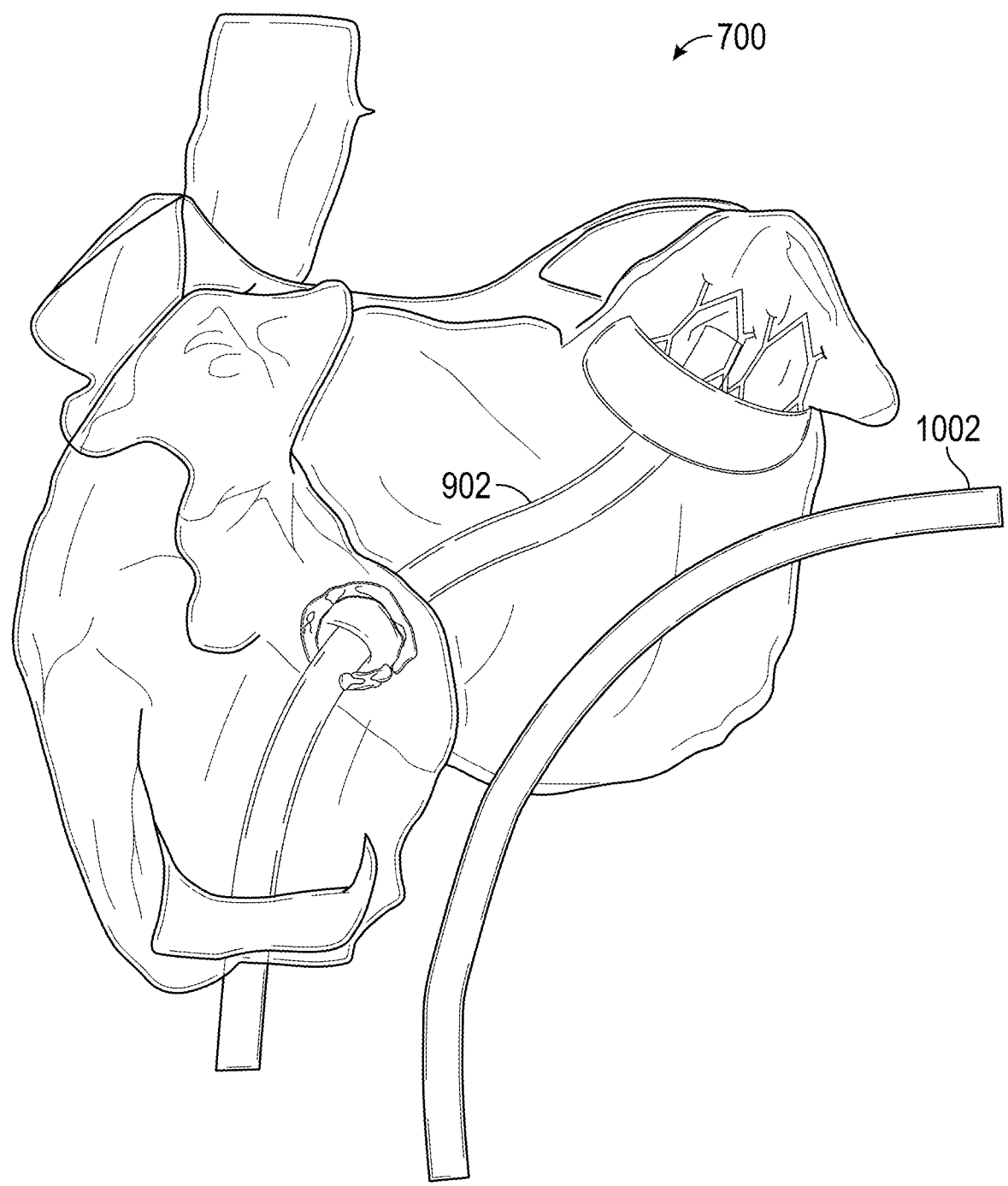
FIG. 10 illustrates a surface model of a catheter with a pre-defined shape along with the determined target trajectory based on FIG. 7, according to certain embodiments.
Figure 11:
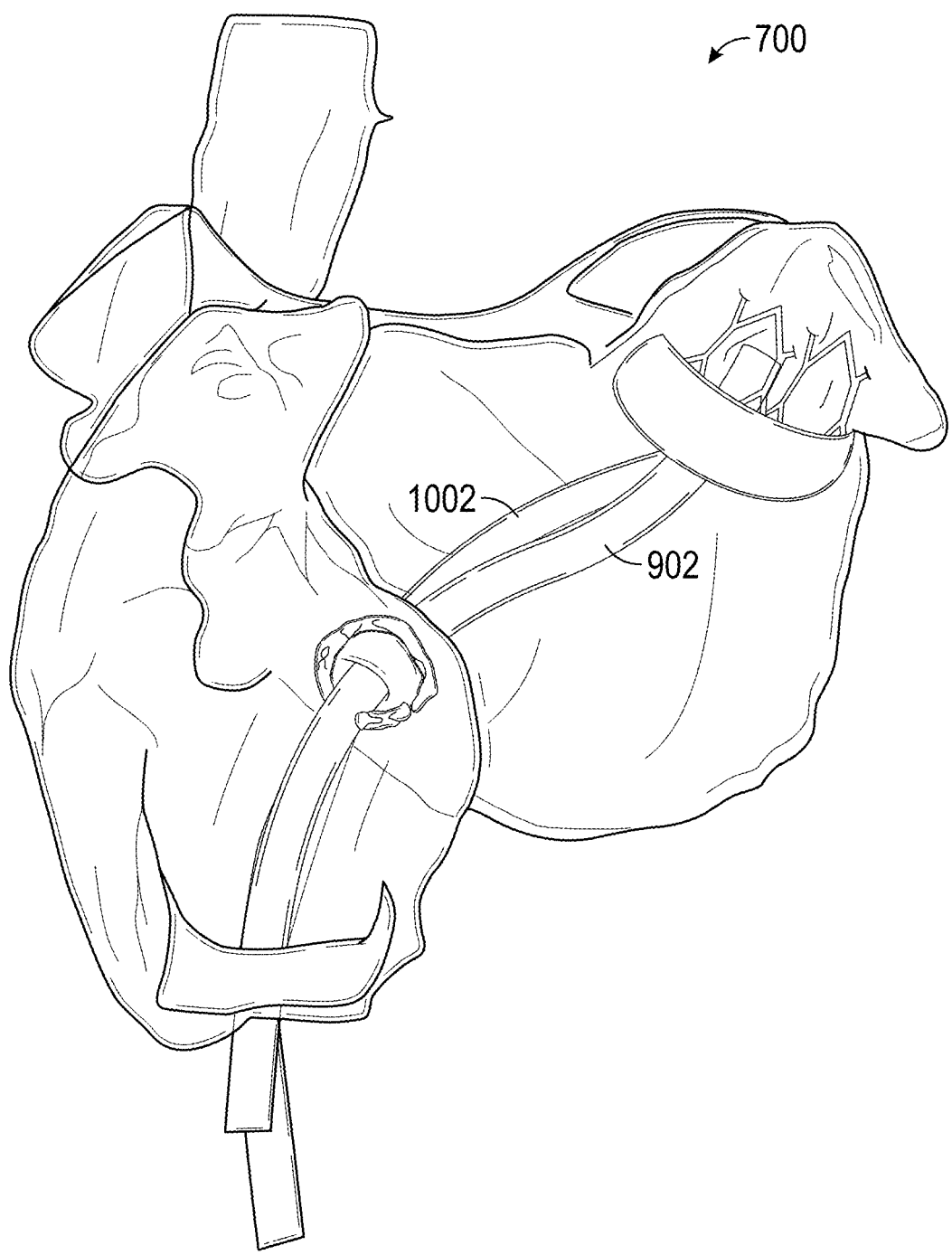
FIG. 11 illustrates the surface model of the catheter of FIG. 10 as registered to the determined target trajectory based on FIG. 7, according to certain embodiments.

2) Once the preferred trajectory has been determined, the execution-planning module 114 may consult the database 106 and determine for each catheter in the database how well its pre-determined shape matches the preferred trajectory. Different approaches are possible. For example, if database 106 contains for each catheter geometric information of the centerline of at least its distal part, the execution-planning module 114 may register this centerline onto the preferred trajectory. A first plurality of points may be defined at regular intervals, to begin with the catheter's distal end. A second plurality of points may be defined at identical intervals, to begin with the planned location of the LAAO device. Next the first and second pluralities may be registered by means of any rigid point set registration algorithm known in the art. Alternatively, if database 106 contains for each catheter geometric information regarding the catheter's outer surface and diameter (or radius), a virtual tube may be created by sweeping a circle with the same diameter along the preferred trajectory. For example, FIG. 9 shows the resulting target trajectory 902, which is shown by sweeping the spline 709 with a circle to produce a tubular surface. Next, the surface model of the catheter may be registered onto the swept surface. For example, FIG. 10 illustrates a surface model of a catheter 1002 with a pre-defined shape. For example, FIG. 11 illustrates the surface model of the catheter 1002 registered to the resulting target trajectory 902. For each catheter, the execution-planning module 114 may compute whether the deviation between the registered centerline or surface model and the preferred trajectory or swept surface, respectively, falls within set tolerances. As output, the execution-planning module 114 may deliver a list of suitable catheters. Alternatively, the execution-planning module 114 may assign to each catheter in the database 106 a score based on said deviation. As output, the module may deliver a list of catheters, each with a score. The execution-planning module 114 may consider only those catheters that are compatible with the implantable device selected by the procedure-plan-acquisition module 110 if compatibility information is available in the database 106. Alternatively or additionally, the execution-planning module may display the catheter's registered centerline or surface model onto a depiction as described below and allow the user to visually assess the suitability of the particular catheter.

Further, in certain aspects, as additional output, the execution-planning module 114 may deliver additional measurements regarding the preferred trajectory and/or catheter, such as a distance between the registered centerline and the center of the FO.

In certain embodiments, the execution-planning module 114 presents one or more of any of the trajectories mentioned above (e.g., both target trajectories and catheter-specific trajectories) in a visual representation of the anatomy. The visual representation may comprise one or more depictions of the medical images and/or a virtual 3D model of the relevant anatomy stored in database 106, generated by image processing module 108, and/or acquired by the data reception module. The visual representation may comprise any combination of 2D and/or 3D views achieved through displaying of image data, volume rendering or surface rendering. The execution-planning module 114 may comprise augmented-reality or virtual-reality capabilities for presenting the trajectories to a user. The execution-planning module 114 may allow the user to specify viewing directions or may impose predefined viewing directions. In certain aspects, the execution-planning module 114, as discussed, further presents additional measurements in the visualization such as regarding the preferred trajectory and/or catheter, such as a distance between a bend and the FO. In certain aspects, the execution-planning module 114, as discussed, further presents a model of a catheter in a patient's anatomy corresponding to the procedure and/or delivery trajectory in the visualization.

Figure 12:
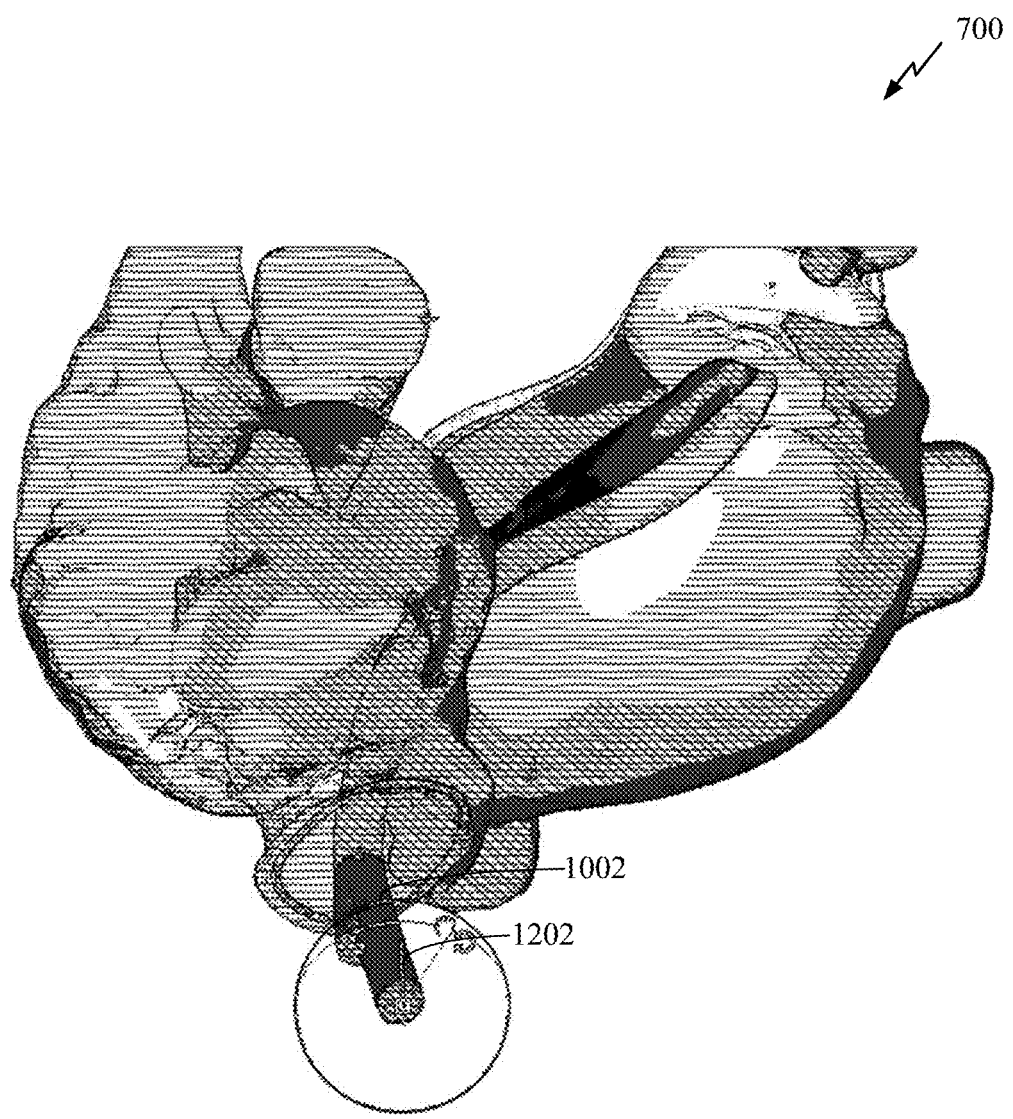
FIG. 12 illustrates an ability to rotate the surface model of the catheter of FIG. 10 as registered to the determined target trajectory based on FIG. 7, according to certain embodiments.

The execution-planning module 114 may present a trajectory by means of trajectory segments (e.g. shown as solid, dashed or dotted 2D lines, curves, cylinders, tubes or the like), optionally connected by nodes (e.g. shown as circles, squares, diamonds, spheres, cubes, etc.). At any step in the process, the execution-planning module 114 may allow the user to interactively move nodes or trajectory segments in the visual representation. The execution-planning module 114 may limit this movement in any appropriate way or make other parts of the trajectory move along with it (e.g. such that the trajectory remains contained in the blood pool volume of the atria, such that the trajectory always passes through the fossa ovalis, such that the trajectory requirements do not have to be overly relaxed, such that a catheter-specific trajectory remains within the capabilities of the catheter, etc.). For catheters with a pre-defined shape, the limitation of the movement may dictate that this shape stay constant, i.e. the movement represent a rigid transformation. Additional limitations may be possible. For example, the execution-planning module 114 may only allow the user to rotate the representation of the catheter around the inflow axis of the IVC, or may limit translation to within the boundaries of the opening of the IVC. For example, FIG. 12 illustrates how the surface model of the catheter 1002 may be rotated around the inflow axis of the IVC 1202. In certain aspects, the execution-planning module 114 may present a trajectory by means of a model of a catheter in a patient's anatomy corresponding to the procedure and/or delivery trajectory.

In certain embodiments, the execution-planning module 114 allows the user to select one of the proposed catheters. Alternatively, the user may decide to return to the procedure-plan-acquisition module 110 to evaluate a different implantable device and/or a different location and/or orientation of the implantable device and re-iterate the process.

As with the image processing module 108, the execution-planning module 114 may be a network-based application which is accessed via a web browser by one or more client devices 104. It may also be a native application installed into the operating system of a computer, such as client device 104 for example. In still other embodiments, the execution-planning module 114 may be a network application which is run as a client/server implementation.

The computing environment also may include an output module 116. In certain embodiments, the optional output module 116 is configured to export the execution plan and/or the procedure plan to a file, or to an intra-operative guidance system. Such a guidance system may overlay the planned trajectory and/or planned location and orientation of the implantable device onto images captured during the intervention, it may provide visual, audible and/or force feedback to the person operating the catheter, or it may robotically steer the catheter along the planned trajectory. The output module 116 may comprise augmented-reality or virtual-reality capabilities for presenting the trajectories to a user. The execution plan may comprise data regarding the selected catheter and/or 3D data of the relevant anatomy and the trajectory of the catheter through the anatomy.

As with the image processing module 108, the output module 116 may be a network-based application which is accessed via a web browser by one or more client devices 104. It may also be a native application installed into the operating system of a computer such as, client device 104 for example. In still other embodiments, the output module 116 may be a network application which is run as a client/server implementation.

Figure 2:
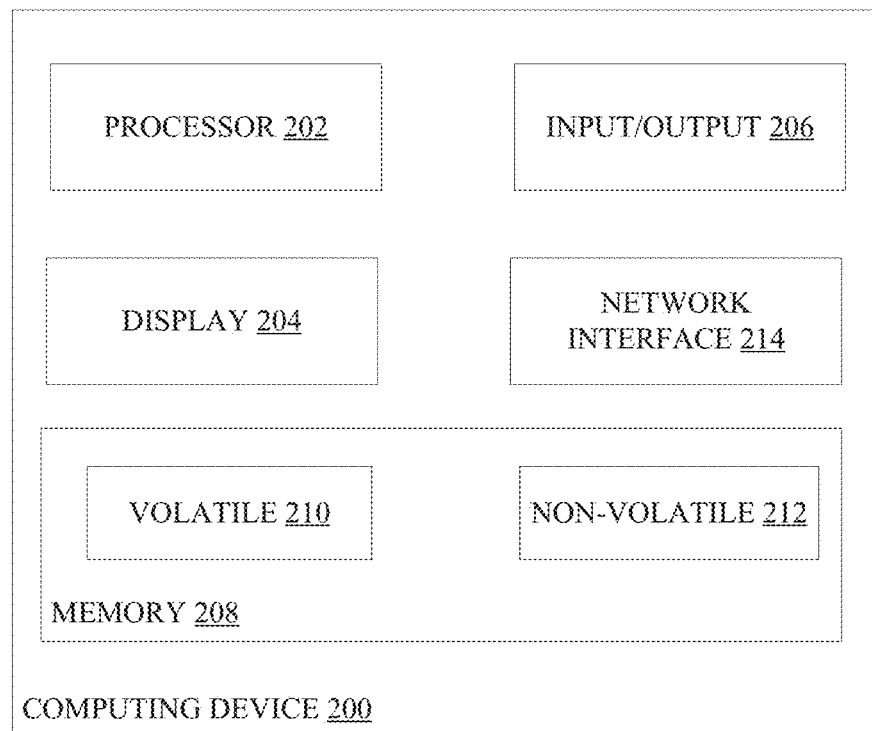
FIG. 2 is a high level system diagram of a computing system that may be used in accordance with one or more embodiments.

Various embodiments of the invention may be implemented using general and/or special purpose computing devices. Turning now to FIG. 2, an example of a computing device 200 suitable for implementing various embodiments of the invention is shown. The computer system 200 may generally take the form of computer hardware configured to execute certain processes and instructions in accordance with various embodiments of one or more embodiments described herein. The computer hardware may be a single computer or it may be multiple computers configured to work together. The computing device 200 includes a processor 202. The processor 202 may be one or more standard personal computer processor such as those designed and/or distributed by Intel, Advanced Micro Devices, Apple, or ARM. The processor 202 may also be a more specialized processor designed specifically for image processing and/or analysis. The computing device 200 may also include a display 204. The display 204 may be a standard computer monitor such as, an LCD monitor as is well known. The display 204 may also take the form of a display integrated into the body of the computing device, for example as with an all-in-one computing device or a tablet computer.

The computing device 200 may also include input/output devices 206. These may include standard peripherals such as keyboards, mice, printers, and other basic I/O software and hardware. The computing device 200 may further include memory 208. The memory 208 may take various forms. For example, the memory 208 may include volatile memory 210. The volatile memory 210 may be some form of random access memory, and may be generally configured to load executable software modules into memory so that the software modules may be executed by the processor 202 in a manner well known in the art. The software modules may be stored in a nonvolatile memory 212. The non-volatile memory 212 may take the form of a hard disk drive, a flash memory, a solid state hard drive or some other form of non-volatile memory. The non-volatile memory 212 may also be used to store non-executable data, such database files and the like.

The computer device 200 also may include a network interface 214. The network interface may take the form of a network interface card and its corresponding software drivers and/or firmware configured to provide the system 200 with access to a network (such as the Internet, for example). The network interface card 214 may be configured to access various different types of networks, such as those described above in connection with FIG. 2. For example the network interface card 214 may be configured to access private networks that are not publicly accessible. The network interface card 214 may also be configured to access wireless networks such using wireless data transfer technologies such as EVDO, WiMAX, or LTE network. Although a single network interface 214 is shown in FIG. 2, multiple network interface cards 214 may be present in order to access different types of networks. In addition, a single network interface card 214 may be configured to allow access to multiple different types of networks.

In general, the computing environment 100 shown in FIG. 1 may generally include one, a few, or many different types of computing devices 200 which work together to carry out various embodiments described below. For example, the computing device 200 may correspond to client device 104. Further, the modules of FIG. 1 may correspond to one or more computing devices 200 (e.g., run on one or more computing devices 200). A skilled artisan will readily appreciate that various different types of computing devices and network configurations may be implemented to carry out the inventive systems and methods disclosed herein.

Figure 5:
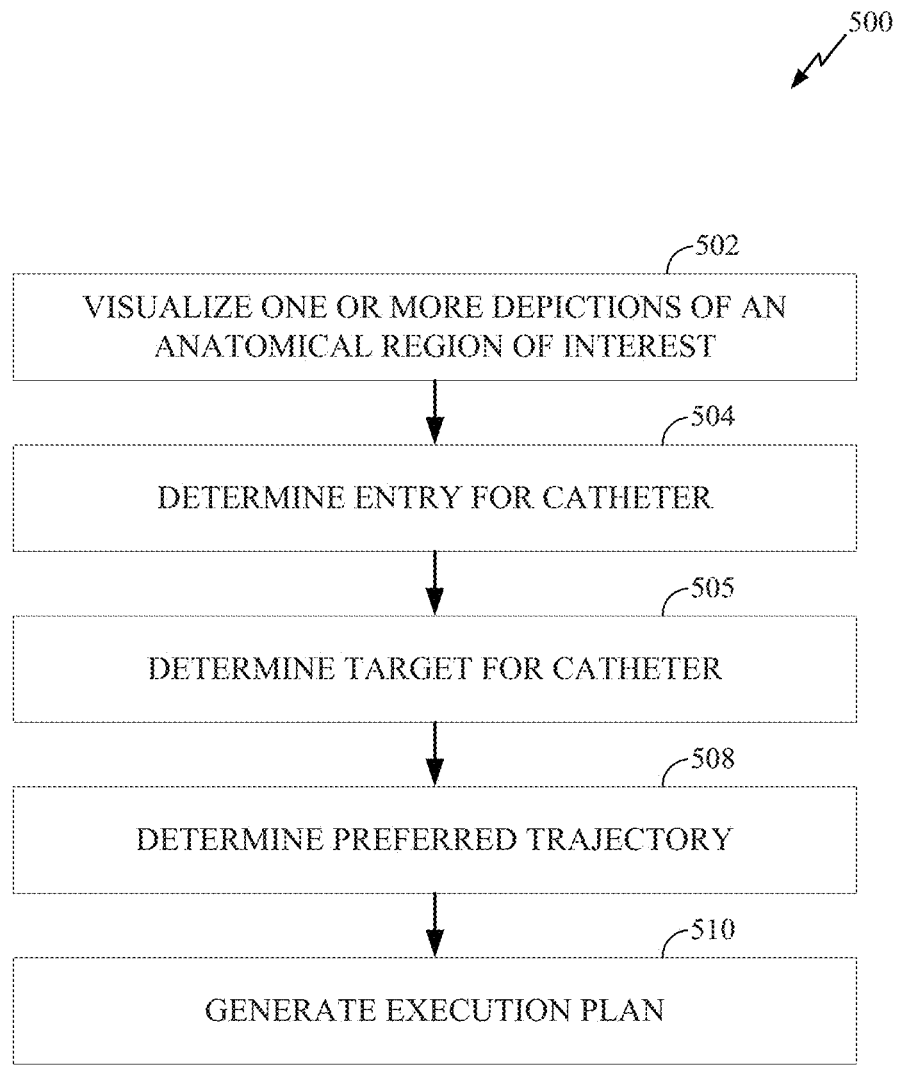
FIG. 5 illustrates a flow chart showing an example process for planning a catheter-based intervention, according to certain embodiments.

FIG. 5 illustrates a flow chart showing an example process 500 for planning a catheter-based intervention. It should be noted that in certain embodiments, process 500 is a computer-implemented process (e.g., by computing environment 100, computing device 200, etc.). Further, certain blocks may be performed automatically, manually by a user of a computing device, or partially manually and partially automatically such as based on input from a user of a computing device.

Process 500 begins at block 502, where the computing device visualizes (e.g., displays) one or more depictions of an anatomical region of interest. For example, the computing device generates a digital model of the anatomical region of interest. Continuing, at block 504, the computing device determines an entry for the catheter. Further, at block 505, the computing device determines a target for the catheter. Continuing, at block 508, the computing device determines a preferred trajectory for a catheter from the entry to the target. Further, at block 510, the computing device generates, based on the preferred trajectory, an execution plan.

Figure 6:
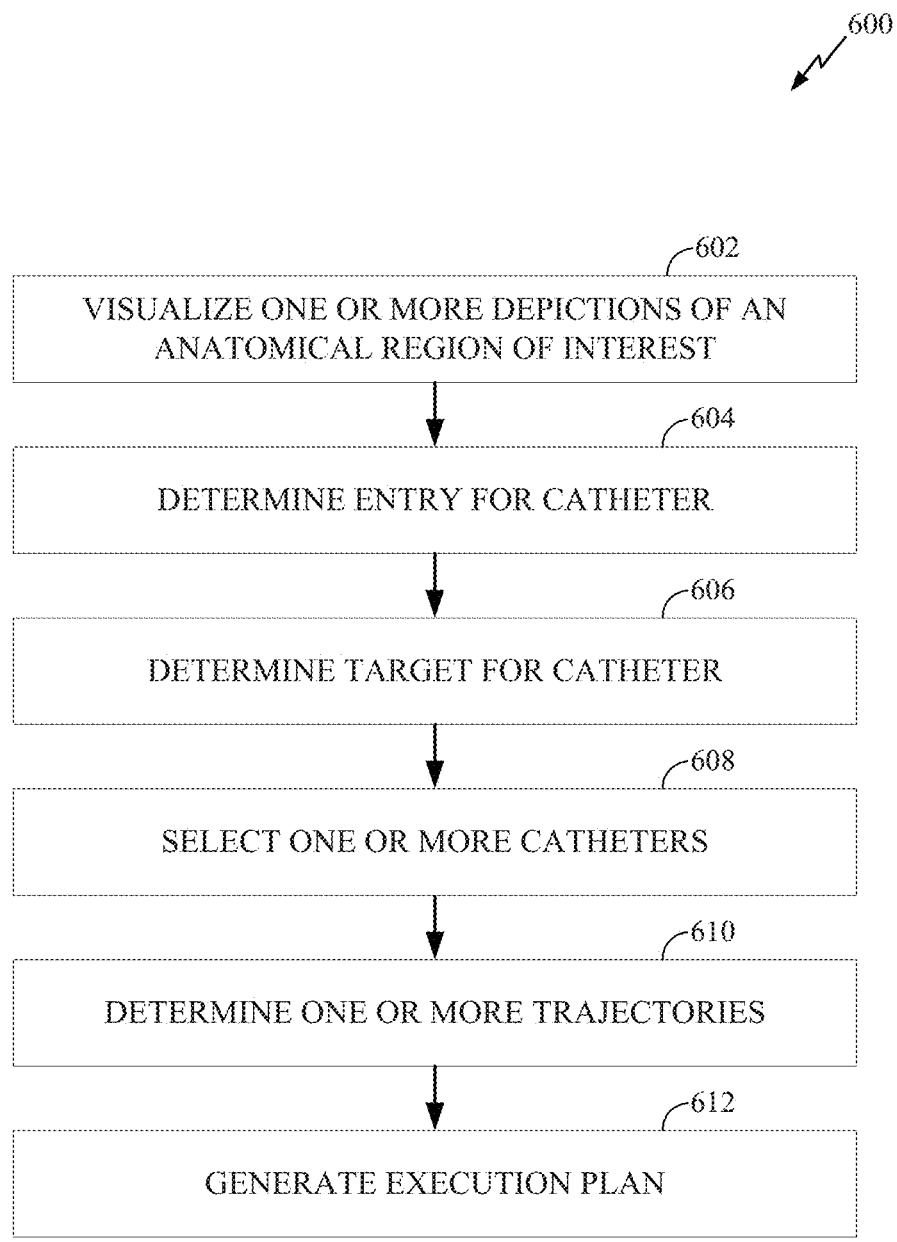
FIG. 6 illustrates a flow chart showing an example process for planning a catheter-based intervention, according to certain embodiments.

FIG. 6 illustrates a flow chart showing an example process 600 for planning a catheter-based intervention. It should be noted that in certain embodiments, process 600 is a computer-implemented process (e.g., by computing environment 100, computing device 200, etc.). Further, certain blocks may be performed automatically, manually by a user of a computing device, or partially manually and partially automatically such as based on input from a user of a computing device.

Process 600 begins at block 602, where the computing device visualizes (e.g., displays) one or more depictions of an anatomical region of interest. For example, the computing device generates a digital model of the anatomical region of interest. Continuing, at block 604, the computing device determines an entry for the catheter. Further, at block 606, the computing device determines a target for the catheter. Continuing, at block 608, the computing device selects from a database one or more catheters suitable/eligible for the catheter-based intervention. Further, at block 610, for each of the one or more catheters, the computing device determines a trajectory from the entry to the target. Further, at block 612, the computing device generates, based on the one or more trajectories, an execution plan.

Figure 13:
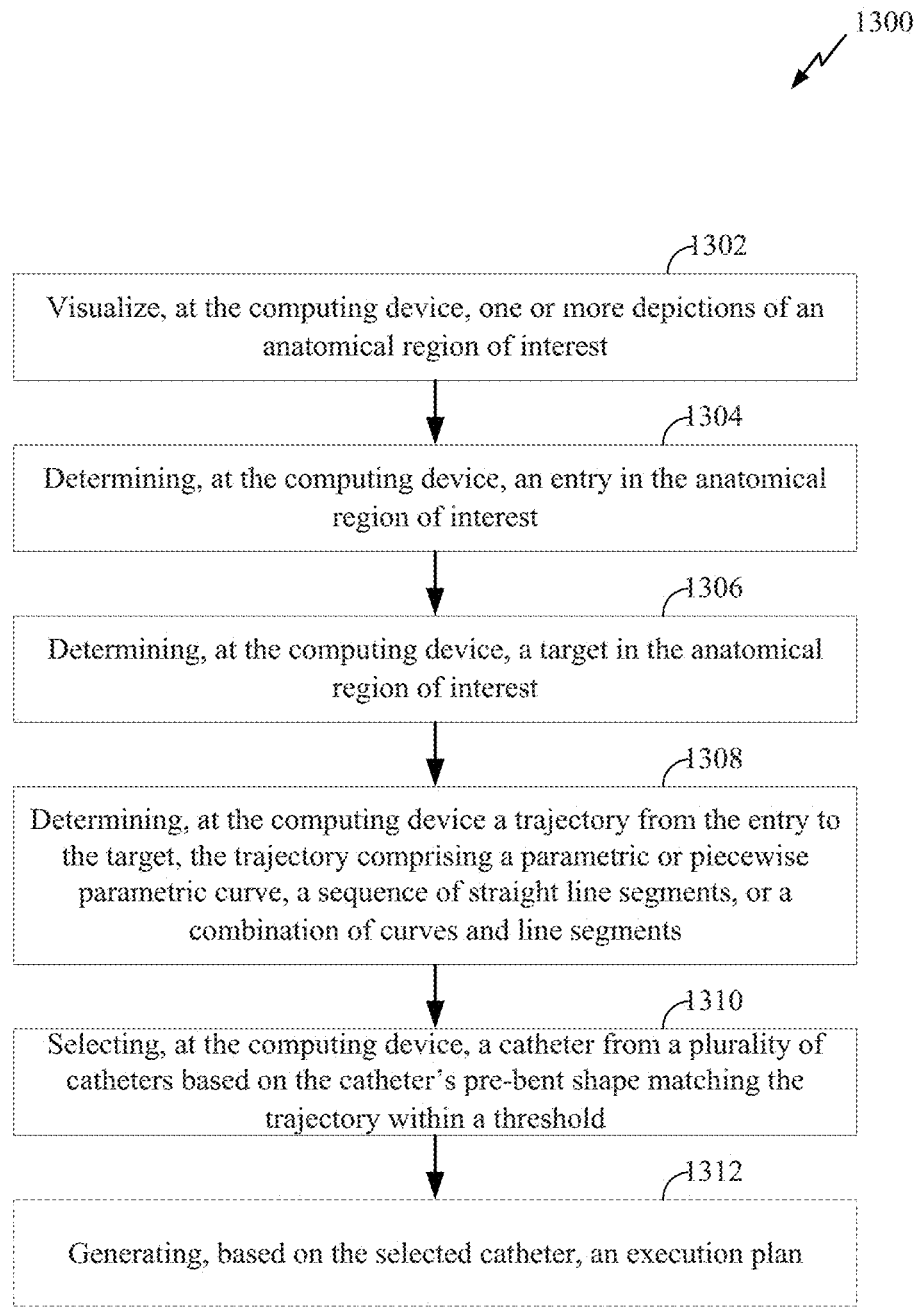
FIG. 13 illustrates a flow chart showing an example process for planning a catheter-based intervention, according to certain embodiments.

FIG. 13 illustrates a flow chart showing an example process 1300 for planning a catheter-based intervention. It should be noted that in certain embodiments, process 1300 is a computer-implemented process (e.g., by computing environment 100, computing device 200, etc.). Further, certain blocks may be performed automatically, manually by a user of a computing device, or partially manually and partially automatically such as based on input from a user of a computing device.

Process 1300 begins at block 1302, where the computing device visualizes (e.g., displays) one or more depictions of an anatomical region of interest. For example, the computing device generates a digital model of the anatomical region of interest.

Process 1300 continues at block 1304 by determining, at the computing device, an entry in the anatomical region of interest.

Process 1300 continues at block 1306 by determining, at the computing device, a target in the anatomical region of interest.

Process 1300 continues at block 1308 by determining, at the computing device a trajectory from the entry to the target, the trajectory comprising a parametric or piecewise parametric curve, a sequence of straight line segments, or a combination of curves and line segments.

Process 1300 continues at block 1310 by selecting, at the computing device, a catheter from a plurality of catheters based on the catheter's pre-bent shape (e.g., best, within a threshold, etc.) matching the trajectory.

Process 1300 continues at optional block 1312 by generating, based on the selected catheter, an execution plan.

In some embodiments, the processes 500 and/or 600 and/or 1300 may be computer-implemented methods. The processes 500 and/or 600 and/or 1300 may be wholly or partly performed by a computing device, a medical practitioner, and/or a non-medical user, such as an engineer or technician.

In some embodiments, the anatomical region of interest may be the heart of a patient, a part of the heart of a patient, and/or the blood pool volume of the heart of a patient or a part of the heart of a patient, such as the right and left atria and/or the LAA.

In some embodiments, the entry may be the IVC, the opening of the IVC in the right atrium or a point within the opening of the IVC in the right atrium, such as its geometric center point.

In some embodiments, the catheter-based intervention may be the delivery of an implantable device and the target may be a planned position of the implantable device in the anatomical region of interest. In some embodiments, the implantable device may be a prosthetic mitral valve, and the planned position of the implantable device may be a location and orientation of the prosthetic mitral valve within the mitral valve of the patient. In some embodiments, the implantable device may be an LAAO device, and the planned position of the implantable device may be a location and orientation of the LAAO device within the LAA of the patient In some embodiments, the one or more depictions of the anatomical region of interest may be 2D and/or 3D visualizations. These may, amongst others, be medical images, volume renderings of medical images, virtual 3D models or combinations thereof.

In some embodiments, visualizing one or more depictions (e.g., block 502 and/or 602 and/or 1302) comprises showing the depictions on a screen of a computing device.

In some embodiments, visualizing one or more depictions of an anatomical region of interest (e.g., block 502 and/or 602 and/or 1302) may further comprise receiving data pertaining to the anatomical region of interest. The data may take the form of medical images of the anatomical region of interest, e.g. the patient's heart or portions of the patient's heart, or of a virtual 3D model of the anatomical region of interest. Medical images may be received from a medical imaging machine, a PACS system, or another form of file transfer. For example, the images may be uploaded by the user from a data carrier to a standalone module or a web-based portal. Virtual 3D models may be received through any form of file transfer. For example, virtual 3D models may be uploaded by the user from a data carrier to a standalone module or to a web-based portal.

In some embodiments, visualizing one or more depictions of an anatomical region of interest (e.g., block 502 and/or 602 and/or 1302) may further comprise converting medical images into one or more virtual 3D models of the relevant anatomy. This process can be automated by means of any automatic segmentation method known in the art. Alternatively or additionally this can be a manual process comprising thresholding, filtering, local mask editing operations, image-processing techniques and the like. For example, the Mimics software by Materialise can be used for this process.

In some embodiments, determining an entry (e.g., block 504 and/or 604 and/or 1304) may comprise determining a point of entry at which a trajectory of a catheter is to enter the anatomical region of interest. Alternatively or additionally, it may comprise determining an area within the anatomical region of interest within which a point of entry should be located. In some embodiments, determining an entry may further comprise determining an entry direction, e.g. a direction to which a trajectory of a catheter should be parallel as it enters the anatomical region of interest.

In some embodiments, an entry may be determined by manually indicating it on one or more of the one or more depictions of the anatomical region of interest.

In some embodiments, determining an entry may comprise identifying in the data pertaining to the anatomical region of interest one or more anatomical landmarks. Anatomical landmarks may be identified manually or automatically by means of any feature-recognition methods known in the art. Anatomical landmarks may be individual points, lines, curves or areas in the anatomical region of interest that may serve to define an entry. For example, the opening of the IVC in the right atrium may be identified as an area within which the point of entry should be located. For example, the geometric center of the opening of the IVC in the right atrium may be identified as the point of entry. For example, the centerline of the section of the IVC closest to the right atrium may be identified to determine the entry direction.

In some embodiments, determining an entry may further comprise visualizing the entry in one or more of the one or more depictions of the anatomical region of interest. This may comprise overlaying onto one or more of the one or more depictions a visual marker, such as a dot, a circle, a disk, a square, a diamond or the like to indicate a single point of entry. Additionally or alternatively, it may comprise overlaying onto one or more of the one or more depictions a visual marker, such as a closed polyline, a closed curve, a closed spline curve, a colored transparent, semitransparent or opaque shape, a hatched shape or the like to indicate an area or region within which a suitable point of entry may be located. For example, the opening of the IVC in the right atrium may be visualized on a virtual 3D model of the blood pool volume of the right atrium as the area comprising all suitable points of entry by means of a polyline around its circumference. An entry direction may be visualized by overlaying onto one or more of the one or more depictions a visual marker, such as a trajectory segment, a solid line, a dotted line, a dashed line, optionally with a marker at one of its endpoints, such as an arrow, a dot, a square or the like.

In some embodiments, determining an entry (e.g., block 504 and/or 604 and/or 1304) may further comprise manually editing the entry, the point of entry, the area of entry and/or the entry direction. This may, for example, be achieved by means of interactively moving one or part of any of the visual markers described above.

In some embodiments, determining a target (e.g., block 505 and/or 606 and/or 1306) may comprise determining a target point at which a trajectory of a catheter is to terminate. Alternatively or additionally, it may comprise determining an area within the anatomical region of interest within which a target point should be located. In some embodiments, determining a target may further comprise determining a target direction, e.g. a direction to which the final section of a trajectory of a catheter should be parallel.

In some embodiments, a target may be determined by manually indicating it on one or more of the one or more depictions of the anatomical region of interest.

In some embodiments, determining a target may comprise identifying in the data pertaining to the anatomical region of interest one or more anatomical landmarks. Anatomical landmarks may be identified manually or automatically by means of any feature-recognition methods known in the art. Anatomical landmarks may be individual points, lines, curves or areas in the anatomical region of interest that may serve to define a target. For example, the annulus of the mitral valve may be identified as an area within which the target point should be located. For example, the geometric center of the annulus of the mitral valve may be identified as the target point. For example, the normal vector of the plane best fitting the mitral valve's annulus may be identified to determine the target direction. For example, the ostium of the LAA may be identified as an area within which the target point should be located. For example, the geometric center of the ostium of the LAA may be identified as the target point. For example, the centerline of the LAA's lumen may be identified to determine the target direction.

In some embodiments, determining a target may comprise visualizing it in one or more of the one or more depictions of the anatomical region of interest. A target may be visualized by overlaying onto one or more of the one or more depictions a visual marker, such as a dot, a circle, a disk, a square, a diamond or the like to indicate a single point. Additionally or alternatively, it may comprise overlaying onto one or more of the one or more depictions a visual marker, such as a closed polyline, a closed curve, a closed spline curve, a colored transparent, semitransparent or opaque shape, a hatched shape or the like to indicate an area or region within which a suitable target may be located. Additionally or alternatively, it may comprise overlaying onto one or more of the one or more depictions a visual marker, such as a trajectory segment, a solid line, a dotted line, a dashed line, optionally with a marker at one of its endpoints, such as an arrow, a dot, a square or the like, to indicate a direction in which the catheter should reach the target.

In some embodiments, determining a target may further comprise manually editing the target. This may, for example, be achieved by means of interactively moving one or part of any of the visual markers described above.

Additionally or alternatively, in those cases where the catheter-based intervention is the delivery of an implantable device, visualizing a target may further comprise visualizing the implantable device in its planned position. For example, a prosthetic mitral valve may be visualized in a virtual 3D model of the native mitral valve as a cylinder or as a virtual 3D model of the prosthetic device. A target point may further be visualized by means of a dot or a sphere on the valve's deployment axis. A target direction may further be visualized by means of a line parallel to the valve's deployment axis. For example, an LAAO device may be visualized in a virtual 3D model of the LAA as a cylinder or as a virtual 3D model of the LAAO device. A target point may further be visualized by means of a dot or a sphere on the device's deployment axis. A target direction may further be visualized by means of a line parallel to the device's deployment axis.

In some embodiments in which the catheter-based intervention is the delivery of an implantable device, determining the target may further comprise loading and/or visualizing a virtual 3D model of the implantable device from a file, database, library, network location or data carrier. Additionally or alternatively, it may comprise loading a procedure plan from a file, network location or data carrier. Such a procedure plan may comprise data concerning the device to be implanted, such as its type, brand and/or size, and its planned location and orientation with respect to the patient's anatomy.

In some embodiments, determining a target may further comprise manually designating and/or editing the planned position of an implantable device, e.g. its location and/or orientation with respect to the patient's anatomy. This may, for example, be achieved by means of interactively moving the visual representation of the implantable device, and/or one or more visual markers attached to it. Target point and/or target direction may follow the changes made to the planned position of the implantable device.

In some embodiments, processes 500 and/or 600 and/or 1300 for planning a catheter-based intervention may further comprise an additional block (e.g., after block 505/606/1306 and before block 508/608/1308) of determining one or more local passages. The additional block may comprise identifying in the data pertaining to the anatomical region of interest one or more anatomical landmarks. Anatomical landmarks may be identified manually or automatically by means of any feature-recognition methods known in the art. Anatomical landmarks may be individual points, lines, curves or areas in the anatomical region of interest that may serve to define local points and/or directions of passage for the trajectory. For example, the boundary of the fossa ovalis may be identified as the boundary of an area through which the trajectory should pass. For example, the geometric center of the fossa ovalis may be identified as a point through which the trajectory should pass. For example, the normal vector of the plane best fitting the fossa ovalis may be identified to determine a direction to which the trajectory should locally be parallel.

In some embodiments, determining a local passage may comprise visualizing it in one or more of the one or more depictions of the anatomical region of interest. A local passage may be visualized by overlaying onto one or more of the one or more depictions a visual marker, such as a dot, a circle, a disk, a square, a diamond or the like to indicate a single point. Additionally or alternatively, it may comprise overlaying onto one or more of the one or more depictions a visual marker, such as a closed polyline, a closed curve, a closed spline curve, a colored transparent, semitransparent or opaque shape, a hatched shape or the like to indicate an area or region within which a suitable local passage may be located. Additionally or alternatively, it may comprise overlaying onto one or more of the one or more depictions a visual marker, such as a trajectory segment, a solid line, a dotted line, a dashed line, optionally with a marker at one of its endpoints, such as an arrow, a dot, a square or the like, to indicate a direction to which the catheter should be parallel as it passes the local passage.

In some embodiments, determining a local passage may further comprise manually editing the local passage. This may, for example, be achieved by means of interactively moving one or part of any of the visual markers described above.

In some embodiments, block 508 of determining a preferred trajectory for a catheter from the entry to the target may comprise determining a trajectory as a sequence of one or more trajectory segments through the anatomical region of interest from the entry to the target. The number of trajectory segments can be chosen freely by the user or can be a predetermined number, such as, for example, 3 or any other whole number. The number may depend on the type of catheter-based intervention or the types of available catheters. For example, if only catheters are available with n locations of controlled bending, the number of trajectory segments may be set at n+1.

If the determined entry defines a single point of entry, the first trajectory segment may have a starting point coinciding with or close to the point of entry. If the determined entry defines an area, the point of entry may be a point within that area. If the determined entry also defines an entry direction, the first trajectory segment may be parallel or substantially parallel to the entry direction.

If the determined target defines a single point, the final trajectory segment may have an end point coinciding with or close to the target point. If the determined target defines an area, the end point may be a point within that area. If the visualized target also defines a target direction, the final trajectory segment may be parallel or substantially parallel to the target direction.

In some embodiments, determining a preferred trajectory for a catheter in block 508 comprises determining a contiguous sequence of trajectory segments. There may be one or more requirements or constraints with which, in an ideal situation, the sequence of trajectory segments complies. For example, the first trajectory segment may start at a determined entry point and be parallel to a determined entry direction, the final trajectory segment may end at a determined target point and be parallel to a determined target direction, and one or more intermediate trajectory segments may pass through identified local points of passage and/or be parallel to identified local directions of passage. For example, a first trajectory segment may start at the IVC and may ideally coincide with the central inflow axis of the IVC, e.g. it has one endpoint in the center of the opening of the IVC in the right atrium and a direction tangential to the central longitudinal axis of the IVC at that point. For example, a second trajectory segment may ideally perforate the fossa ovalis at the geometric center point of the fossa ovalis and may ideally be parallel to the central axis of the fossa ovalis, e.g. the axis through the geometric center of the fossa ovalis and parallel to the normal vector to the plane best fitting the fossa ovalis. For example, a third trajectory segment may end at the planned position of an implantable device and may ideally be parallel to the deployment axis of the implantable device. For example, all trajectory segments should be fully contained within the blood pool volume of the heart, except for the section where the second trajectory segment perforates the fossa ovalis.

In a typical situation, it may not be possible to reconcile all of these requirements. Determining a preferred trajectory may therefore be based on an order of priority in which these requirements may be relaxed and/or a degree to which these requirements may be relaxed. For example, the process 500 may keep the end point and the direction of the final trajectory segment fixed. It may prioritize to first relax the requirement of the second trajectory segment being parallel to the central axis of the fossa ovalis, optionally within a predetermined angular range. It may prioritize to then relax the requirement of the second trajectory segment passing through the geometric center point of the fossa ovalis, optionally within a predetermined distance range. It may prioritize to next relax the requirement of the first trajectory segment being parallel to the IVC inflow axis, optionally within a predetermined angular range. It may prioritize to next relax the requirement of the first trajectory segment having its starting point in the center of the opening of the IVC, optionally within a predetermined distance range. The process 500 may follow a heuristic approach. Alternatively, the process 500 may search for the sequence of trajectory segments that optimizes a certain target function, e.g. the sequence that minimizes a weighted average of how far the requirements need to be relaxed, or the sequence that minimizes the angles between consecutive trajectory segments. Any suitable optimization techniques known in the art may be used to optimize the sequence of trajectory segments for the chosen target function.

Other priorities or combinations of fixed and relaxed requirements are possible. For example, the process 500 may keep all requirements fixed except the second trajectory segment being parallel to the central axis of the fossa ovalis. As illustrated in FIG. 3C, the second trajectory segment may then be determined as the trajectory segment that connects a point on the central inflow axis of the IVC 322, represented as a cylinder, with a point on the deployment axis of the implantable device 315, represented as a cylinder, and passes through the geometric center point 370 of the fossa ovalis. This trajectory segment can be determined by constructing a plane 372 through the central inflow axis of the IVC 322 and the geometric center point 370 of the fossa ovalis, then determining the point 374 at which the deployment axis of the implantable device 315 intersects this plane 372, then creating a line through this point 374 and the geometric center point 370 of the fossa ovalis, then determining point 376 where this line intersects the central inflow axis of the IVC 322 and then creating a trajectory segment that connects both intersection points 374 and 376. Alternatively, this trajectory segment can be determined by constructing a plane 378 through the deployment axis of the implantable device 315 and the geometric center point 370 of the fossa ovalis, then determining the point 376 at which the central inflow axis of the implantable device 322 intersects this plane 378, then creating a line through this point 376 and the geometric center point 370 of the fossa ovalis, then determining point 374 where this line intersects the deployment axis of the implantable device 315 and then creating a trajectory segment that connects both intersection points 374 and 376. Alternatively, the same result can be obtained by constructing a first plane 372 through the central inflow axis of the IVC 322 and the geometric center point 370 of the fossa ovalis, constructing a second plane 378 through the deployment axis of the implantable device 315 and the geometric center point 370 of the fossa ovalis, determining the intersection line of these two planes, and creating a trajectory segment between the points 374 and 376 where this intersection line intersects with the central inflow axis of the IVC 322 and the deployment axis of the implantable device 315.

In some embodiments, determining a preferred trajectory for a catheter in block 508 may further comprise visualizing the preferred trajectory in one or more of the one or more depictions of the anatomical region of interest. This may comprise overlaying onto one or more of the one or more depictions a visual marker, such as a trajectory segment, a solid line, dashed line, dotted line, cylinder or the like for each of the trajectory segments in the determined contiguous sequence of trajectory segments. Optionally, the points between the trajectory segments may be visualized as nodes, e.g. by overlaying onto one or more of the one or more depictions visual markers, such as circles, squares, diamonds, spheres, cubes, etc.

In some embodiments, determining a preferred trajectory may further comprise manually editing the trajectory. This may, for example, be achieved by means of interactively moving one or part of any of the visual markers described above.

In some embodiments, block 510 of generating, based on the preferred trajectory, an execution plan may comprise evaluating for one or more catheters or types of catheters whether or to what extent the preferred trajectory can be achieved with that catheter. This may involve comparing for a catheter the distances between its locations of controlled bending with the lengths of the corresponding trajectory segments of the preferred trajectory, and/or comparing for a catheter the angles between consecutive trajectory segments with the ranges of motion of the catheter's corresponding locations of controlled bending. Alternatively or additionally, the block 510 may comprise computing for a catheter the trajectory that is still within the catheter's capabilities and comes closest to the preferred trajectory, computing to what extent its trajectory would have to deviate from the preferred trajectory and optionally assigning a score based on that deviation, e.g. as a polynomial function of the angles and/or the differences in length between corresponding sections of the preferred trajectory and the catheter's closest-matching trajectory.

In some embodiments, block 510 may comprise loading from a file, a database or any kind of data carrier data relating to the one or more catheters to be evaluated. Alternatively, it may comprise assigning values to the parameters of a generic parametric model of a catheter, such as number of locations of controlled bending, range of motion for each bend, distance from the distal end to the first bend, distances between consecutive bends, etc.

In some embodiments, evaluating one or more catheters or types of catheters may comprise retrieving from a database (e.g., database 106) data concerning one or more catheters or types of catheters. Such data may comprise data describing the suitability of a catheter for the envisaged catheter-based intervention. For example, if the catheter-based intervention is the delivery of an implantable device, the data may describe the compatibility of the catheter with the implantable device. The data may further comprise geometric data, such as data describing the locations along the catheter of locations of controlled bending, the distances between such locations of controlled bending and/or the ranges of motion at such locations of controlled bending. In some embodiments, evaluating one or more catheters or catheter types may comprise selecting from a database of catheters only those catheters that are suitable for the envisaged catheter-based intervention (e.g. those catheters compatible with the planned device to be implanted) and evaluating each of those catheters. The outcome of the evaluation can, for example, be a list of suitable catheters or catheter types, or a list of catheters or catheter types, each with a score determined as described above.

Block 510 may further comprise selecting, based on the evaluation, a preferred catheter. This selection may be performed by a user, such as a medical professional or a technically skilled user, such as a technician or engineer, or may be fully automated based on pre-defined criteria. For example, the catheter with the highest or lowest score may be selected. If only one catheter has been evaluated, selecting a preferred catheter may comprise either approving or declining it based on its evaluation. The pre-defined criteria may include physician preferences, such as preferred supplier, preferred catheter type, etc.

Block 510 may further comprise generating an execution plan. The execution plan may comprise any combination of data relating to the patient, the anatomical region of interest, the preferred catheter, the preferred trajectory, the catheter's closest-matching trajectory, the catheter's score, etc. An execution plan may be stored to a file. It may take the format of a report. The report may comprise instructions for executing the catheter-based intervention, e.g. how many degrees to bend the catheter at each location of controlled bending or how many degrees to twist the catheter between locations of controlled bending. Alternatively or additionally, it may be visualized on the display of a computing device. Alternatively or additionally, it may serve as input for an intra-operative guidance system. For example, an intra-operative imaging system may be equipped with the functionality to register data in the execution plan regarding the anatomical region of interest onto medical images captured intra-operatively so as to overlay the preferred trajectory or the catheter's closest-matching trajectory onto the intra-operative images. For example, the execution plan may serve as input to a robotic surgical device. For anatomical parts that vary in shape over time, the execution plan may comprise data relating to different variations of shape, e.g. data relating to the systole and data relating to the diastole.

In some embodiments, block 608 of selecting from a database one or more catheters eligible for the catheter-based intervention may comprise consulting a database (e.g., database 106) containing data concerning different catheters or catheter types. The data may relate to any one or more of the following: catheter brand, type, capabilities, eligibility for one or more catheter-based interventions, compatibility with one or more implantable devices, etc. The data may contain an identification of each catheter and may describe the technical capabilities of each catheter. The technical capabilities may comprise one or more of catheter-specific geometric information, such as the catheter's dimensions, the locations and shapes of any curves along its length, the locations along its length where the catheter's operator may control its bending and/or the range of motion and curvature of each of these bends. The database may also contain data pertaining to one or more implantable devices. The data may contain an identification of each implantable device. The database may also contain compatibility data, describing which implantable devices are compatible with which catheters. Block 608 may further comprise selecting, based on information regarding the envisaged catheter-based intervention and data stored in the database one or more eligible catheters, e.g. catheters that might be suitable for execution of the envisaged intervention. For example, if the envisaged intervention is the delivery of an implantable device of a certain brand and type, the result of block 608 may be a list of all catheters in the database that are compatible with the given brand and type of implantable device.

In some embodiments, block 610 of for each of the one or more catheters, determining and optionally visualizing in one or more of the one or more depictions a trajectory from the entry to the target may comprise determining for each of the catheters identified in block 608 as eligible one or more possible trajectories from the entry to the target based on the catheter-specific geometric information stored in the database.

In some embodiments, determining a trajectory for a catheter in block 610 comprises determining a contiguous sequence of trajectory segments. There may be one or more requirements with which, in an ideal situation, the sequence of trajectory segments complies. For example, the first trajectory segment may start at a determined entry point and be parallel to a determined entry direction, the final trajectory segment may end at a determined target point and be parallel to a determined target direction, and one or more trajectory segments may pass through identified local points of passage and/or be parallel to identified local directions of passage. For example, a first trajectory segment may start at the IVC and may ideally coincide with the central inflow axis of the IVC, e.g. it has one endpoint in the center of the opening of the IVC in the right atrium and a direction tangential to the central longitudinal axis of the IVC at that point. For example, a second trajectory segment may ideally perforate the fossa ovalis at the geometric center point of the fossa ovalis and may ideally be parallel to the central axis of the fossa ovalis, e.g. the axis through the geometric center of the fossa ovalis and parallel to the normal vector to the plane best fitting the fossa ovalis. For example, a third trajectory segment may end at the planned position of an implantable device and may ideally be parallel to the deployment axis of the implantable device. For example, all trajectory segments should be fully contained within the blood pool volume of the heart, except for the section where the second trajectory segment perforates the fossa ovalis.

In a typical situation, it may not be possible to reconcile all of these requirements. Each of the one or more trajectories may therefore be evaluated against the requirements described above. For each of the requirements, the trajectory's deviation from the ideal situation may be computed, e.g. as the angle between the IVC's central inflow axis and the corresponding section of the catheter, the angle between the fossa ovalis' central axis and the corresponding section of the catheter, the angle between the implantable device's deployment axis and the corresponding section of the catheter, the shortest distance between the center of the opening of the IVC and the catheter, the distance between the geometric center of the fossa ovalis and the point where the catheter intersects the septum, the distance between the center point of the implantable device and the axis of the most distal section of the catheter, etc. A target function may be defined as a polynomial function of these deviations and a catheter-specific optimal trajectory may be determined by using any suitable optimizing algorithm known in the art.

The coefficients of the polynomial function may penalize certain deviations more than others. A score may be assigned to each trajectory, e.g. based on the value of the target function and for each eligible catheter a catheter-specific optimal trajectory may be selected based on the score. Any suitable optimization techniques known in the art may be used to optimize the catheter-specific trajectory for the target function and come to a catheter-specific optimal trajectory.

Limits may be set to the search space, e.g. by imposing maximum values to one or more of the computed deviations, and/or by monitoring that the entire trajectory is entirely contained within the blood pool volume of the right and left atrium. Catheters that are not able to follow a trajectory from the entry through imposed local points of passage to the target that is entirely contained within the blood pool volume may be filtered out.

In some embodiments, block 610 of for each of the one or more catheters, determining a trajectory from the entry to the target may further comprise visualizing in one or more of the one or more depictions a trajectory. Any of the trajectories mentioned above may be shown on the display of a computing device in one or more of the one or more depictions of the anatomical region of interest. A trajectory may be presented by means of trajectory segments (e.g. shown as solid, dashed or dotted 2D lines, curves, cylinders or tubes), optionally connected by nodes (e.g. shown as circles, squares, diamonds, spheres, cubes, etc.). In some embodiments, the user may be allowed to interactively move nodes or trajectory segments in the visual representation. This movement may be limited in any appropriate way or other parts of the trajectory may move along (e.g. such that the trajectory remain contained in the blood pool volume of the atria, such that the trajectory always pass through the fossa ovalis, such that a catheter-specific trajectory remain within the capabilities of the catheter, etc.).

In some embodiments, block 612 of generating, based on the one or more trajectories, an execution plan may comprise selecting from the group of eligible catheters a preferred catheter. This selection may be performed by a user, such as a medical professional or a technically skilled user, such as a technician or engineer, or may be fully automated based on pre-defined criteria. For example, the catheter with the catheter-specific optimal trajectory with the highest score may be selected. If only one catheter has been evaluated, selecting a preferred catheter may comprise either approving or declining it, e.g. based on the score of its catheter-specific optimal trajectory. The pre-defined criteria may include physician preferences, such as preferred supplier, preferred catheter type, etc.

Block 612 may further comprise generating an execution plan. The execution plan may comprise any combination of data relating to the patient, the anatomical region of interest, the selected catheter, the catheter's optimal trajectory, the trajectory's score, etc. An execution plan may be stored to a file. It may take the format of a report. The report may comprise instructions for executing the catheter-based intervention, e.g. how many degrees to bend the catheter at each location of controlled bending or how many degrees to twist the catheter between locations of controlled bending. Alternatively or additionally, it may be visualized on the display of a computing device. Alternatively or additionally, it may serve as input for an intra-operative guidance system. For example, an intra-operative imaging system may be equipped with the functionality to register data in the execution plan regarding the anatomical region of interest onto medical images captured intra-operatively so as to overlay the catheter's optimal trajectory onto the intra-operative images. For example, the execution plan may serve as input to a robotic surgical device. For anatomical parts that vary in shape over time, the execution plan may comprise data relating to different variations of shape, e.g. data relating to the systole and data relating to the diastole.

In some embodiments, block 1308 of determining a trajectory from the entry to the target may comprise determining a trajectory as a parametric or piecewise parametric curve, as a sequence of one or more line segments or as a combination of curves and line segments through the anatomical region of interest from the entry to the target via the local passages, if any. In certain embodiments, the number of trajectory segments can be chosen freely by the user or can be a predetermined number, such as, for example, 1, 2, 3 or any other whole number. In certain embodiments, the number may depend on the type of catheter-based intervention or the types of available catheters. For example, if only catheters are available with n pre-determined bends, the number of trajectory segments may be set at n+1.

In certain embodiments, if the determined entry defines a single point of entry, the trajectory or its first trajectory segment may have a starting point coinciding with or close to the point of entry. In certain embodiments, if the determined entry defines an area, the point of entry may be a point within that area. In certain embodiments, if the determined entry also defines an entry direction, the trajectory or the first trajectory segment may be parallel or substantially parallel to the entry direction in its starting point.

In certain embodiments, if the determined target defines a single point, the trajectory or its final trajectory segment may have an end point coinciding with or close to the target point. In certain embodiments, if the determined target defines an area, the end point may be a point within that area. In certain embodiments, if the visualized target also defines a target direction, the trajectory or the final trajectory segment may be parallel or substantially parallel to the target direction in its end point.

In some embodiments, determining a trajectory may comprise defining a parametric or piecewise parametric curve, such as a spline, from the entry point, through each of the local passage points, if any, to the target point. Determining a trajectory may further comprise defining the parametric or piecewise parametric curve such that it is parallel to the entry direction in the entry point, such that it is parallel to a passage direction in a passage point, and/or such that it is parallel to the target direction in the target point.

In some embodiments, determining a preferred trajectory for a catheter in block 1308 may further comprise visualizing the preferred trajectory in one or more of the one or more depictions of the anatomical region of interest. This may comprise overlaying onto one or more of the one or more depictions a visual marker, such as a trajectory segment, a solid line, dashed line, dotted line, cylinder or the like for each of the trajectory segments in the determined contiguous sequence of trajectory segments. Optionally, the points between the trajectory segments may be visualized as nodes, e.g. by overlaying onto one or more of the one or more depictions visual markers, such as circles, squares, diamonds, spheres, cubes, etc.

In some embodiments, determining a preferred trajectory may further comprise manually editing the trajectory. This may, for example, be achieved by means of interactively moving one or part of any of the visual markers described above.

In some embodiments, block 1310 of selecting, based on the preferred trajectory, a catheter from a plurality of catheters may comprise evaluating for one or more catheters or types of catheters whether or to what extent the catheter's pre-determined shape matches the preferred trajectory. This may involve registering the catheter's pre-determined shape onto the preferred trajectory. The registration may be based on the catheter's centerline and the preferred trajectory, or on a surface model of the catheter and a tubular surface obtained by sweeping the preferred trajectory with a circle having the same diameter as the catheter. The evaluation may further involve computing the deviation between the catheter's shape and the preferred trajectory and optionally assigning a score based on that deviation.

In some embodiments, block 1310 may comprise loading from a file, a database or any kind of data carrier data relating to the one or more catheters to be evaluated.

In some embodiments, evaluating one or more catheters or types of catheters may comprise retrieving from a database (e.g., database 106) data concerning one or more catheters or types of catheters. Such data may comprise data describing the suitability of a catheter for the envisaged catheter-based intervention. For example, if the catheter-based intervention is the delivery of an implantable device, the data may describe the compatibility of the catheter with the implantable device. The data may further comprise geometric data, such as a surface model of the catheter, its centerline and/or its diameter or radius. In some embodiments, evaluating one or more catheters or catheter types may comprise selecting from a database of catheters only those catheters that are suitable for the envisaged catheter-based intervention (e.g. those catheters compatible with the planned device to be implanted) and evaluating each of those catheters. The outcome of the evaluation can, for example, be a list of suitable catheters or catheter types, or a list of catheters or catheter types, each with a score determined as described above.

In some embodiments, the evaluation may further comprise visualizing the catheter in the one or more depictions of the anatomical region of interest, e.g., by means of a virtual surface model. The evaluation may further comprise editing, by the user, the position of the catheter in the anatomical region of interest. Limitations may be imposed on the editing capabilities. For example, if the entry comprises an entry direction (e.g., the inflow axis of the IVC), only rotation around this entry direction may be allowed. For example, if the entry comprises an area (e.g., the opening of the IVC), only translation within this area may be allowed.

Block 1310 may further comprise selecting, based on the evaluation, a preferred catheter. This selection may be performed by a user, such as a medical professional or a technically skilled user, such as a technician or engineer, or may be fully automated based on pre-defined criteria. For example, the catheter with the highest or lowest score may be selected. If only one catheter has been evaluated, selecting a preferred catheter may comprise either approving or declining it based on its evaluation. The pre-defined criteria may include physician preferences, such as preferred supplier, preferred catheter type, etc. In some embodiments, the catheter is selected based on the deviation (e.g., the catheter with the least deviation is selected, a catheter having less than a threshold deviation is selected, a catheter having less than a threshold deviation is selected that also meets another criteria (e.g., material, cost, etc.)).

Optional block 1312 may comprise generating an execution plan. The execution plan may comprise any combination of data relating to the patient, the anatomical region of interest, the preferred catheter, the preferred trajectory, the catheter's score, etc. An execution plan may be stored to a file. It may take the format of a report. The report may comprise instructions for executing the catheter-based intervention, e.g. where to pierce the FO. Alternatively or additionally, it may be visualized on the display of a computing device. Alternatively or additionally, it may serve as input for an intra-operative guidance system. For example, an intra-operative imaging system may be equipped with the functionality to register data in the execution plan regarding the anatomical region of interest onto medical images captured intra-operatively so as to overlay the preferred trajectory or the catheter's shape onto the intra-operative images. For example, the execution plan may serve as input to a robotic surgical device. For anatomical parts that vary in shape over time, the execution plan may comprise data relating to different variations of shape, e.g. data relating to the systole and data relating to the diastole.

In some embodiments, the processes 500 and/or 600 and/or 1300 described herein may further comprise an initial block (e.g., prior to block 502/602/1302) of selecting one or more approaches. This selecting block may comprise selecting where the catheter should enter the patient's body and what route it should follow to reach the anatomical region of interest. For example, the user may choose one or more approaches from the group of transapical delivery, transseptal delivery through the femoral artery and transseptal delivery through the subclavian artery.

When the user selects more than one approach, blocks 502-510 and/or 602-612 and/or 1302-1312 may be repeated for each approach. The processes 500 and/or 600 and/or 1300 described herein may then further comprise a final block (e.g., after block 510/612/1312) of selecting a preferred approach. This selecting block may comprise comparing the outcomes of blocks 502-510 and/or 602-612 and/or 1302-1312 between the different approaches and selecting one approach. The selection can be made automatically, e.g. based on the score of each approach's preferred catheter's catheter-specific optimal trajectory. The selection can also be made by a user, e.g. a technical user, such as a technician or engineer, e.g. based on the same objective criterion. The selection can also be made by a medical professional, who can take additional medical concerns into consideration.

Instead of starting from data relating to a specific patient, the systems and methods described herein may also be applied on statistical data. Various kinds of statistical models are known in the art, such as statistical shape models, active shape models, active appearance models and the like. This allows users to evaluate the suitability of a certain catheter type with respect to the broader patient population. For example, a user may use the systems or apply the methods on any instance of a statistical model, such as an instance representing an average patient, or may investigate the 90th percentile of the population. This may help engineers design catheters that are suited for a larger part of the patient population or help develop families of particular catheter types in limited numbers of sizes. Blocks 502 and/or 602 and/or 1302 may then further comprise creating one or more instances of a statistical model, e.g. by selecting parameter values for the model's parameter vector.

Alternatively, the systems and methods described herein may be applied on a plurality of data sets, relating to a plurality of patients from a certain patient population.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Further, one or more blocks/steps may be removed or added. For example, only portions of process 500 and/or 600 and/or 1300 may be performed in certain embodiments.

Various embodiments disclosed herein provide for the use of a computer system to perform certain features. A skilled artisan will readily appreciate that these embodiments may be implemented using numerous different types of computing devices, including both general-purpose and/or special-purpose computing system environments or configurations. Examples of well-known computing systems, environments, and/or configurations that may be suitable for use in connection with the embodiments set forth above may include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. These devices may include stored instructions, which, when executed by a microprocessor in the computing device, cause the computer device to perform specified actions to carry out the instructions. As used herein, instructions refer to computer-implemented steps for processing information in the system. Instructions can be implemented in software, firmware or hardware and include any type of programmed step undertaken by components of the system.

A microprocessor may be any conventional general-purpose single- or multi-chip microprocessor such as a Pentium® processor, a Pentium® Pro processor, an 8051 processor, a MIPS® processor, a Power PC® processor, or an Alpha® processor. In addition, the microprocessor may be any conventional special-purpose microprocessor such as a digital signal processor or a graphics processor. The microprocessor typically has conventional address lines, conventional data lines, and one or more conventional control lines.

Aspects and embodiments of the inventions disclosed herein may be implemented as a method, apparatus or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

What is claimed is:

1. A computer-based method of planning a catheter-based intervention, the method comprising:
obtaining, at a computing device, a model of an anatomical region of interest;
determining, at the computing device, an entry in the anatomical region of interest;
determining, at the computing device, a target in the anatomical region of interest;
determining, at the computing device, a trajectory from the entry to the target, the trajectory comprising a parametric or piecewise parametric curve, a sequence of straight line segments, or a combination of curves and line segments; and
selecting, at the computing device, a catheter from a plurality of catheters,
wherein selecting the catheter comprises:
obtaining geometric information of an outer surface and radius of each of the plurality of catheters;
for each of the plurality of catheters, generating a virtual tube along the trajectory having the corresponding radius;
for each of the plurality of catheters, registering the corresponding outer surface to the corresponding virtual tube;
for each of the plurality of catheters, measuring a deviation between the registered corresponding outer surface and the corresponding virtual tube; and
selecting, among the plurality of catheters, the catheter having the smallest deviation between the registered corresponding outer surface and the corresponding virtual tube.

2. The method of claim 1, wherein the model of the anatomical region of interest comprises at least one of a virtual 3D model of the anatomical region of interest or a medical image of the anatomical region of interest.

3. The method of claim 1, wherein the catheter comprises a device delivery sheath having a pre-determined shape.

4. The method of claim 1, wherein the catheter has one or more predetermined bends.

5. The method of claim 1, wherein determining the trajectory comprises determining the trajectory based on one or more constraints, wherein the one or more constraints comprise one or more operational constraints indicating at least one or more positions within the anatomical region of interest through which the trajectory should pass or one or more tolerances with respect to the one or more positions through which the trajectory should pass.

6. The method of claim 5, wherein the one or more operational constraints comprise one or more of:
at least a portion of the trajectory starting at a first feature of the anatomical region of interest and being tangential to an axis of the first feature within a first tolerance;
at least a portion of the trajectory perforating a second feature of the anatomical region of interest at a geometric center point of the second feature within a second tolerance;
at least a portion of the trajectory ending at the target and being parallel to an axis of the target within a third tolerance; or
at least a portion of the trajectory ending at a geometric center point of a third feature of the anatomical region of interest and being parallel to a centerline of the third feature within a fourth tolerance.

7. The method of claim 6, wherein:
the first feature is an inferior vena cava (IVC) or a superior vena cava (SVC);
the axis of the first feature comprises a central inflow axis of the IVC or SVC;
the second feature is a fossa ovalis;
the target comprises a planned position of an implantable device;

the axis of the target comprises a deployment axis of the implantable device; and the third feature is an ostium of a left atrial appendage.

8. The method of claim 5, wherein the one or more constraints comprise the trajectory being fully contained within a blood pool volume of the anatomical region of interest except for zero or more portions of the trajectory designated to perforate a feature of the anatomical region of interest.

9. The method of claim 1, further comprising visualizing, at the computing device, one or more depictions of the anatomical region of interest and of the catheter as positioned with respect to the trajectory.

10. The method of claim 1, further comprising generating, at the computing device, based on the selected catheter, an execution plan comprising instructions for executing the catheter-based intervention using the catheter.

11. The method of claim 1, wherein selecting the catheter further comprises verifying that the catheter's pre-bent shape matches the trajectory within a threshold.

12. A non-transitory computer-readable medium having computer-executable instructions stored thereon, which, when executed by a processor of a computing device, cause the computing device to perform a method of planning a catheter-based intervention, the method comprising:
obtaining, at a computing device, a model of an anatomical region of interest;
determining, at the computing device, an entry in the anatomical region of interest;
determining, at the computing device, a target in the anatomical region of interest;
determining, at the computing device, a trajectory from the entry to the target, the trajectory comprising a parametric or piecewise parametric curve, a sequence of straight line segments, or a combination of curves and line segments; and
selecting, at the computing device, a catheter from a plurality of catheters,
wherein selecting the catheter comprises:
obtaining geometric information of an outer surface and radius of each of the plurality of catheters;
for each of the plurality of catheters, generating a virtual tube along the trajectory having the corresponding radius;
for each of the plurality of catheters, registering the corresponding outer surface to the corresponding virtual tube;
for each of the plurality of catheters, measuring a deviation between the registered corresponding outer surface and the corresponding virtual tube; and
selecting, among the plurality of catheters, the catheter having the smallest deviation between the registered corresponding outer surface and the corresponding virtual tube.

13. The non-transitory computer-readable medium of claim 12, wherein the model of the anatomical region of interest comprises at least one of a virtual 3D model of the anatomical region of interest or a medical image of the anatomical region of interest.

14. The non-transitory computer-readable medium of claim 12, wherein the catheter comprises a device delivery sheath having a pre-determined shape.

15. A computing device comprising:
a memory; and
a processor configured to perform a method of planning a catheter-based intervention, the method comprising:
obtaining, at a computing device, a model of an anatomical region of interest;
determining, at the computing device, an entry in the anatomical region of interest;
determining, at the computing device, a target in the anatomical region of interest;
determining, at the computing device, a trajectory from the entry to the target, the trajectory comprising a parametric or piecewise parametric curve, a sequence of straight line segments, or a combination of curves and line segments; and
selecting, at the computing device, a catheter from a plurality of catheters,
wherein selecting the catheter comprises:
obtaining geometric information of an outer surface and radius of each of the plurality of catheters;
for each of the plurality of catheters, generating a virtual tube along the trajectory having the corresponding radius;
for each of the plurality of catheters, registering the corresponding outer surface to the corresponding virtual tube;
for each of the plurality of catheters, measuring a deviation between the registered corresponding outer surface and the corresponding virtual tube; and
selecting, among the plurality of catheters, the catheter having the smallest deviation between the registered corresponding outer surface and the corresponding virtual tube.

16. The computing device of claim 15, wherein the model of the anatomical region of interest comprises at least one of a virtual 3D model of the anatomical region of interest or a medical image of the anatomical region of interest.

17. The computing device of claim 15, wherein the catheter comprises a device delivery sheath having a pre-determined shape.

18. The computing device of claim 15, wherein the catheter has one or more predetermined bends.

19. The computing device of claim 15, wherein determining the trajectory comprises determining the trajectory based on one or more constraints, wherein the one or more constraints comprise one or more operational constraints indicating at least one or more positions within the anatomical region of interest through which the trajectory should pass or one or more tolerances with respect to the one or more positions through which the trajectory should pass.

20. The computing device of claim 19, wherein the one or more operational constraints comprise one or more of:
at least a portion of the trajectory starting at a first feature of the anatomical region of interest and being tangential to an axis of the first feature within a first tolerance;
at least a portion of the trajectory perforating a second feature of the anatomical region of interest at a geometric center point of the second feature within a second tolerance;
at least a portion of the trajectory ending at the target and being parallel to an axis of the target within a third tolerance; or
at least a portion of the trajectory ending at a geometric center point of a third feature of the anatomical region of interest and being parallel to a centerline of the third feature within a fourth tolerance.

* * * * *